(12) United States Patent
Al-Jazaeri et al.

(10) Patent No.: US 10,765,847 B1
(45) Date of Patent: Sep. 8, 2020

(54) SINGLE LUMEN DRAINAGE CATHETER WITH EXTENDABLE AND RETRACTABLE DRAINS

(71) Applicants: Ayman H. Al-Jazaeri, Riyadh (SA); Hassan A. Al-Jazaeri, Riyadh (SA)

(72) Inventors: Ayman H. Al-Jazaeri, Riyadh (SA); Hassan A. Al-Jazaeri, Riyadh (SA)

( * ) Notice: Subject to any disclaimer, the term of this patent is extended or adjusted under 35 U.S.C. 154(b) by 0 days.

(21) Appl. No.: 16/709,102

(22) Filed: Dec. 10, 2019

(51) Int. Cl.
*A61M 27/00* (2006.01)
*A61M 1/28* (2006.01)
*A61M 3/02* (2006.01)

(52) U.S. Cl.
CPC .......... *A61M 27/006* (2013.01); *A61M 1/285* (2013.01); *A61M 3/0279* (2013.01); *A61M 2205/32* (2013.01)

(58) Field of Classification Search
CPC .. A61M 27/006; A61M 1/285; A61M 3/0279; A61M 25/0026
See application file for complete search history.

(56) References Cited

U.S. PATENT DOCUMENTS

| | | |
|---|---|---|
| 3,743,439 A | 7/1973 | Cann |
| 4,351,333 A | 9/1982 | Lazarus |
| 4,368,737 A | 1/1983 | Ash |
| 4,377,169 A | 3/1983 | Banks |
| 4,660,571 A | 4/1987 | Hess |
| 4,681,570 A | 7/1987 | Dalton |
| 4,767,400 A | 8/1988 | Miller |
| 4,925,452 A | 5/1990 | Melinyshyn |
| 5,100,395 A | 3/1992 | Rosenberg |
| 5,116,310 A | 5/1992 | Seder |
| 5,254,084 A | 12/1993 | Greary |
| 5,354,279 A * | 10/1994 | Hofling ............. A61M 25/0069 604/164.12 |
| 5,370,610 A | 12/1994 | Reynolds |
| 5,800,414 A | 9/1998 | Cazal |
| 5,891,111 A | 4/1999 | Ismael |
| 6,129,685 A * | 10/2000 | Howard, III ....... A61N 1/36036 600/373 |
| 6,231,570 B1 | 5/2001 | Tu |
| 6,913,589 B2 | 7/2005 | Dextradeur |

(Continued)

FOREIGN PATENT DOCUMENTS

WO    WO 2003030960    4/2003

*Primary Examiner* — Tatyana Zalukaeva
*Assistant Examiner* — Jessica R Arble
(74) *Attorney, Agent, or Firm* — Christopher Pilling

(57) ABSTRACT

A single lumen catheter with extendable and retractable drains for providing improved fluid drainage and irrigation. The catheter generally includes a housing enclosing a single unpartitioned lumen, a plurality of drain ports, and a common drain. A plurality of drains provide a plurality of paths for fluid to flow between the common drain and the exterior of the housing. The plurality of drains are coupled to an internal connector within the single lumen, and are selectively movable via the internal connector and a stylet with a specially shaped end tip between a retracted position in which the drains are enclosed within the lumen and an extended position in which the drains extend through the drain ports to the exterior of the housing. Additionally or alternatively one or more elongated tools or other elements can be coupled to the internal connector and caused to move between retracted and extended positions.

25 Claims, 19 Drawing Sheets

(56) References Cited

U.S. PATENT DOCUMENTS

| | | |
|---|---|---|
| 6,961,602 B2 | 11/2005 | Fuimaono |
| 7,366,557 B2 | 4/2008 | Bautista |
| 7,625,361 B2 | 12/2009 | Suzuki |
| 7,651,520 B2 | 1/2010 | Fischell |
| 7,763,142 B2 | 7/2010 | Watson |
| 8,066,697 B2 | 11/2011 | Zvuloni |
| 8,202,265 B2 | 6/2012 | Boulais |
| 8,221,393 B1 | 7/2012 | Placik |
| 8,409,171 B2 | 4/2013 | Hannon |
| 8,827,944 B2 | 9/2014 | Sevrain |
| 8,920,404 B2 | 12/2014 | Diofiore |
| 9,126,013 B2 | 9/2015 | Watanabe |
| 9,126,020 B2 | 9/2015 | Farhangnia |
| 9,248,254 B2 | 2/2016 | Dehnad |
| 9,314,299 B2 | 4/2016 | Fang |
| 9,750,422 B2 | 9/2017 | Zino |
| 2003/0135147 A1 | 7/2003 | Rosenberg |
| 2008/0033396 A1 | 2/2008 | Danek |
| 2009/0024084 A1 | 1/2009 | Khosla |
| 2010/0305509 A1 | 12/2010 | Osypka |
| 2012/0078159 A1 | 3/2012 | Wilson |
| 2012/0179144 A1 | 7/2012 | Carleo |
| 2012/0323175 A1 | 12/2012 | Vogelbaum |
| 2014/0058315 A1 | 2/2014 | Gupta |
| 2014/0163532 A1* | 6/2014 | Cornet ............. A61M 25/0071 604/543 |
| 2014/0194716 A1 | 7/2014 | Diep |
| 2015/0040893 A1* | 2/2015 | Besseler ........... A61M 15/0071 128/200.21 |
| 2015/0343175 A1 | 12/2015 | Braga |

* cited by examiner

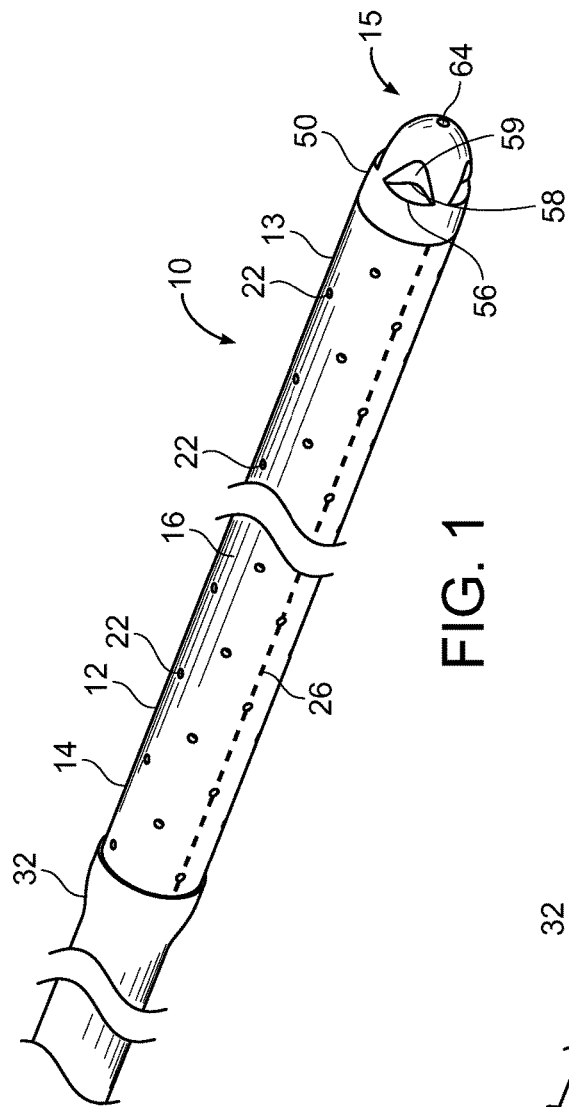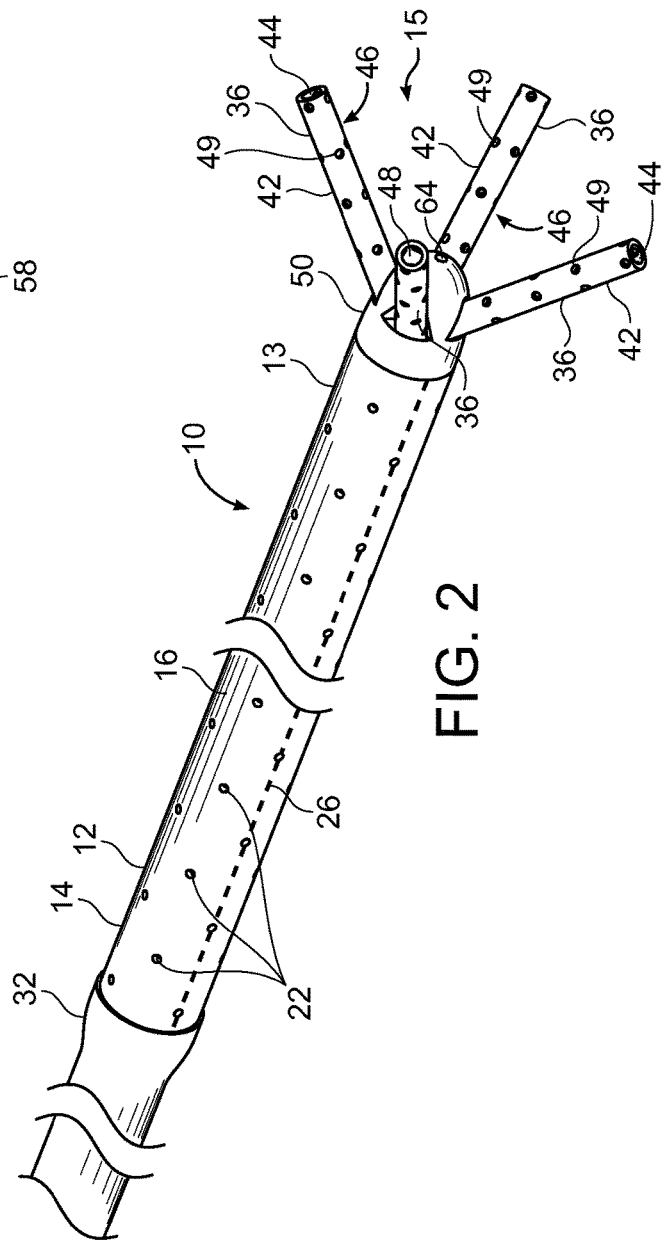

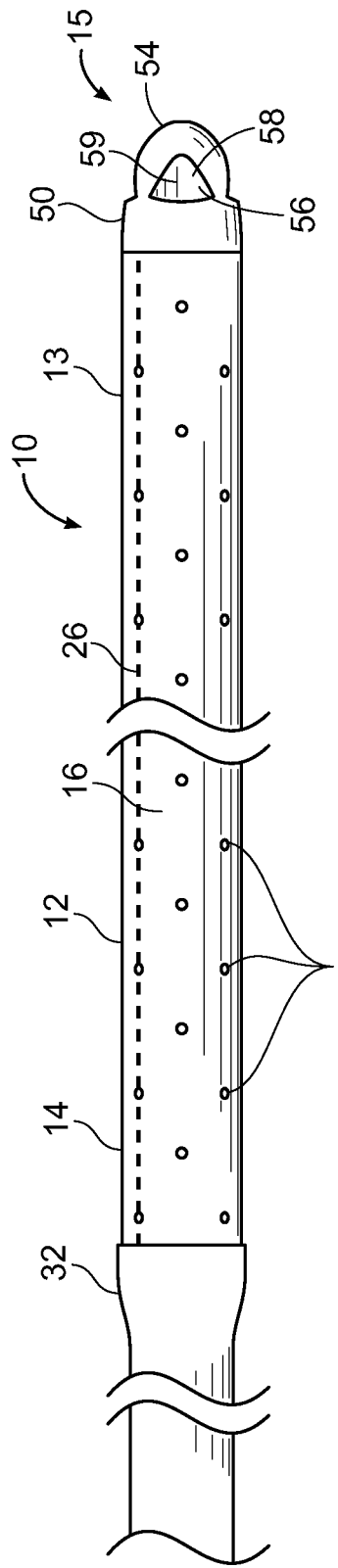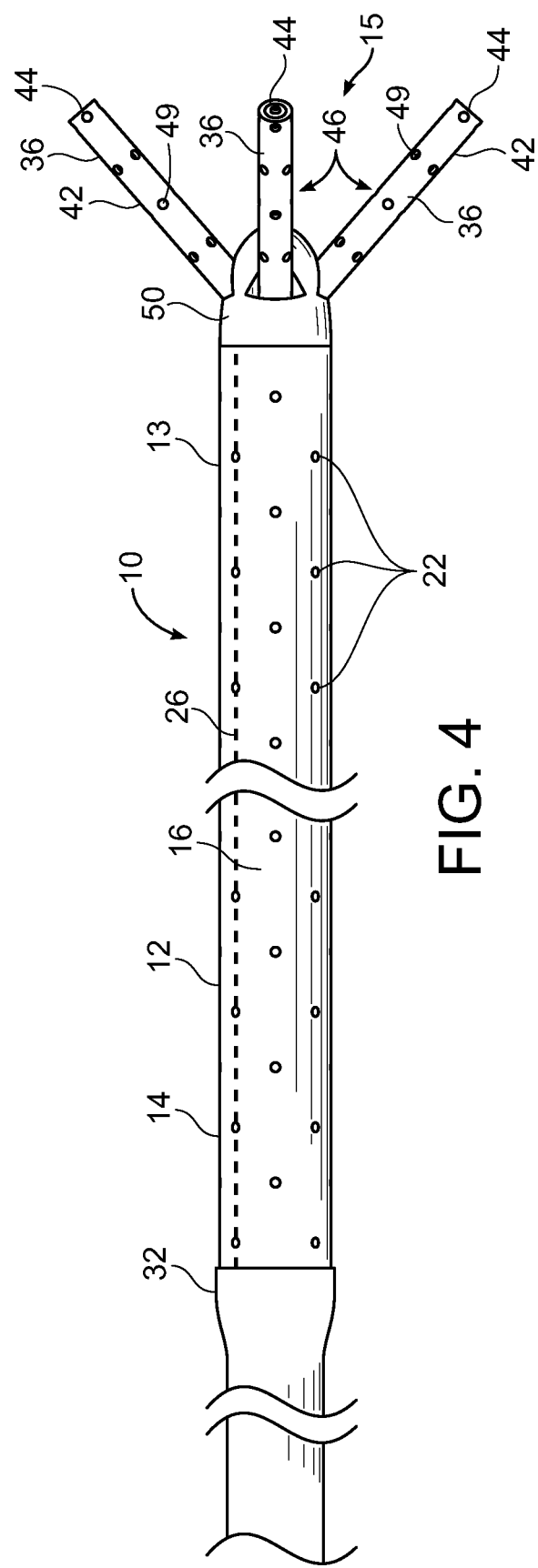

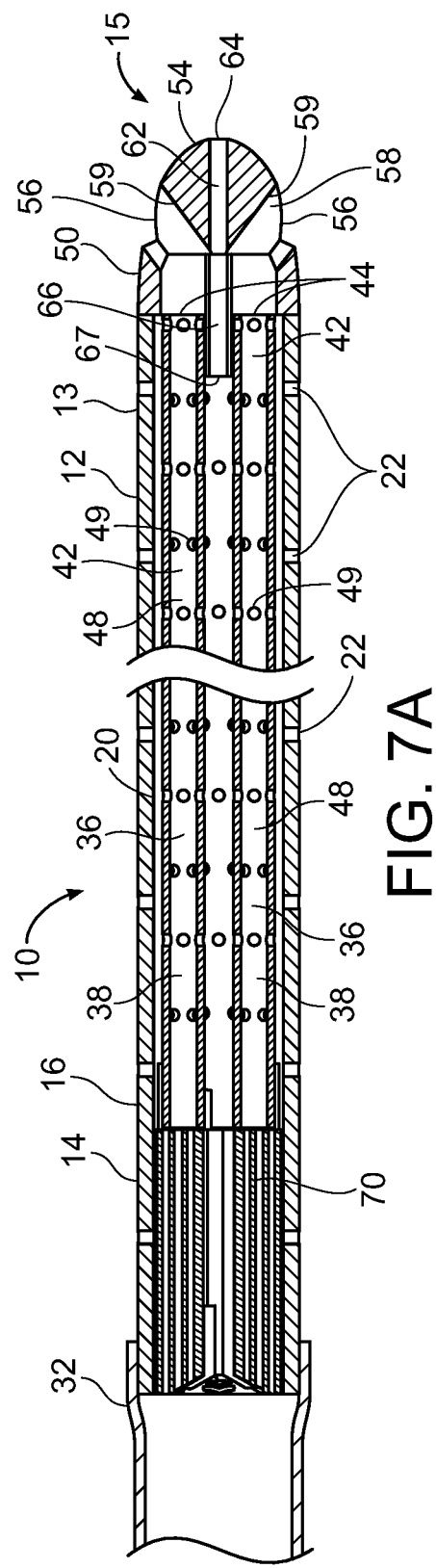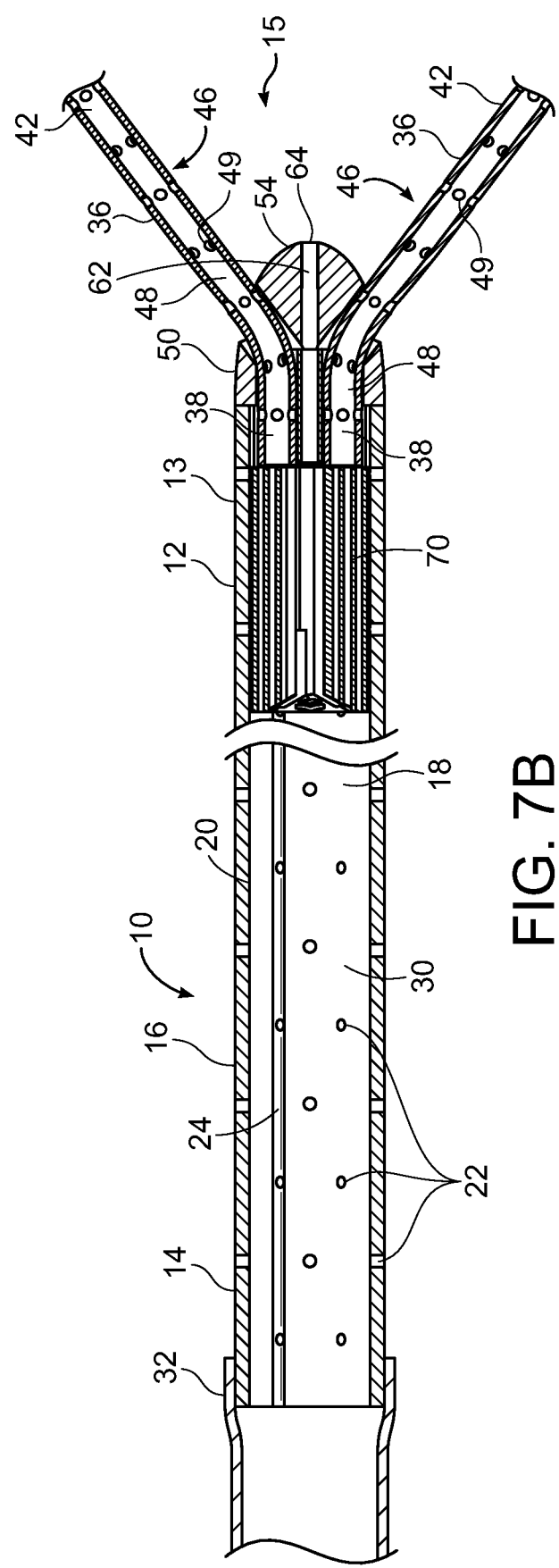
FIG. 7A
FIG. 7B

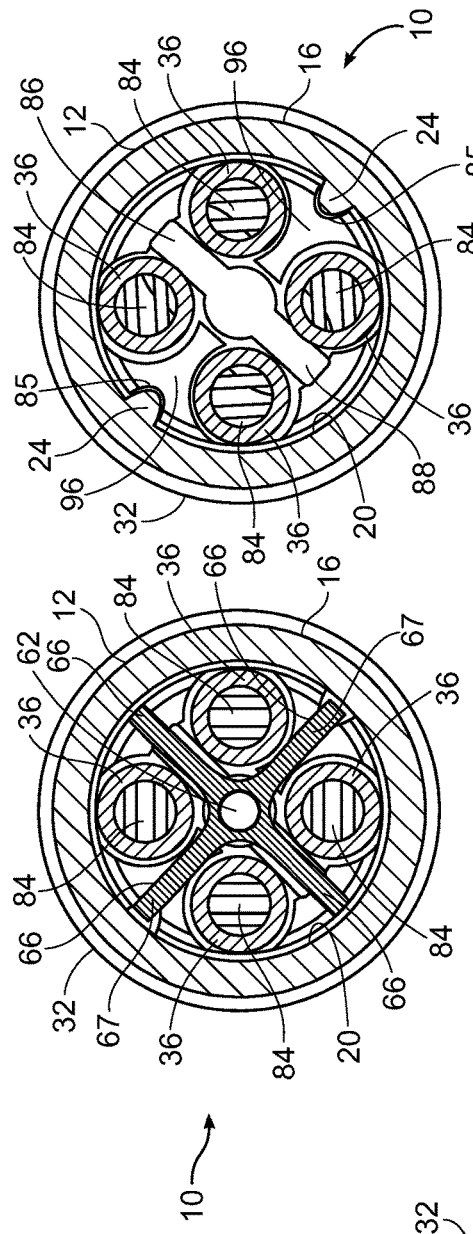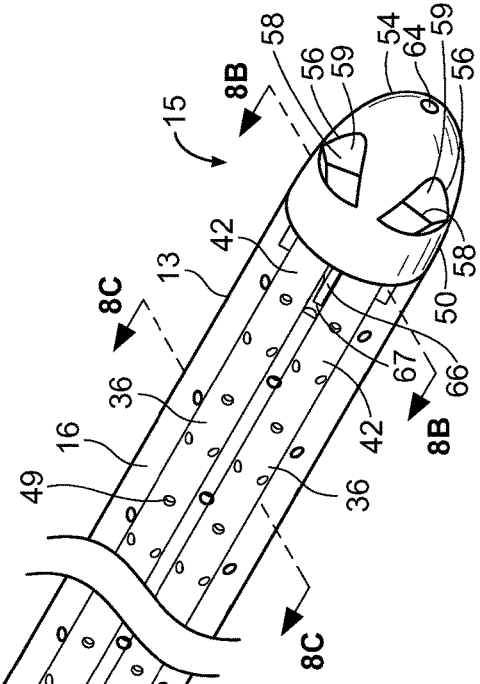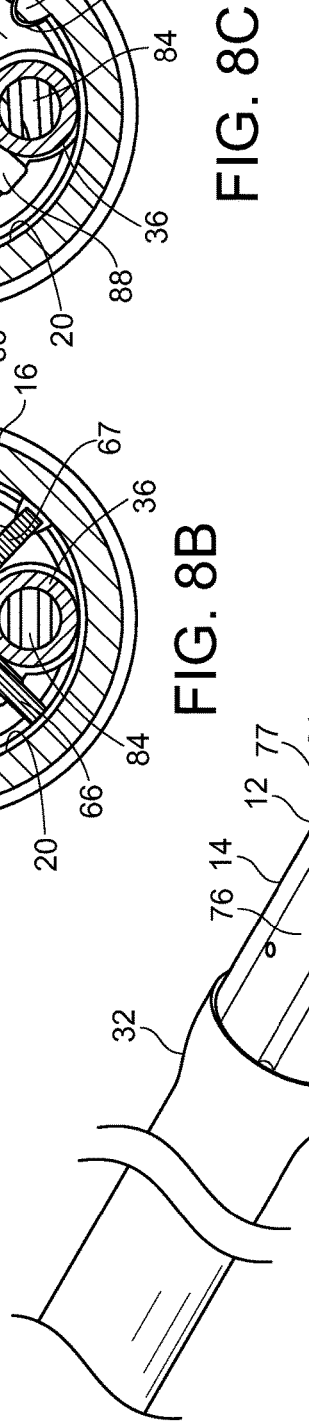

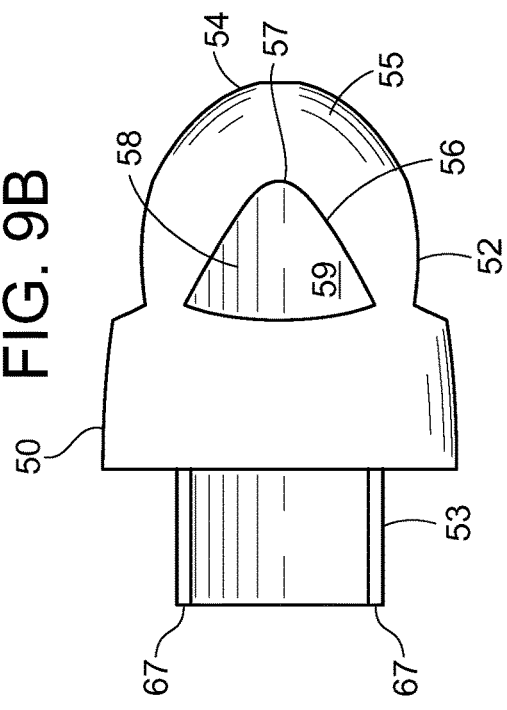
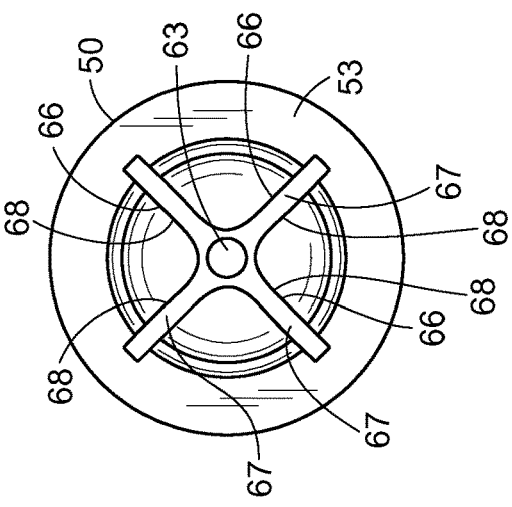
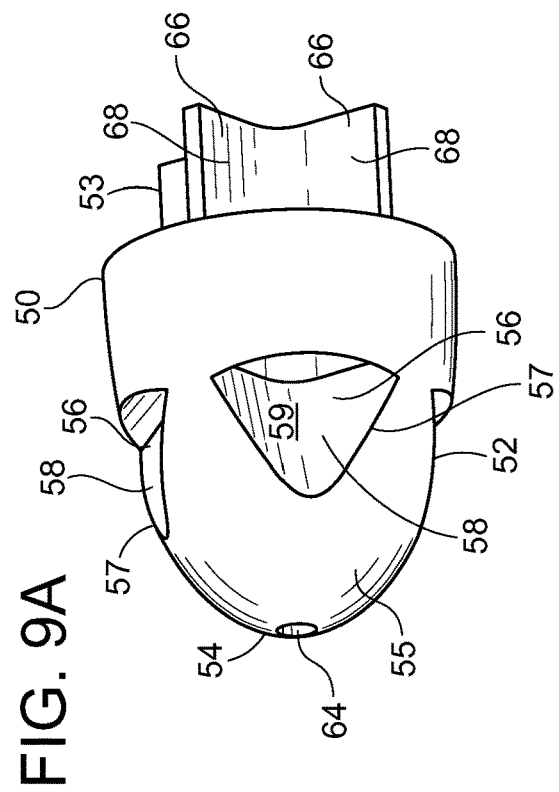
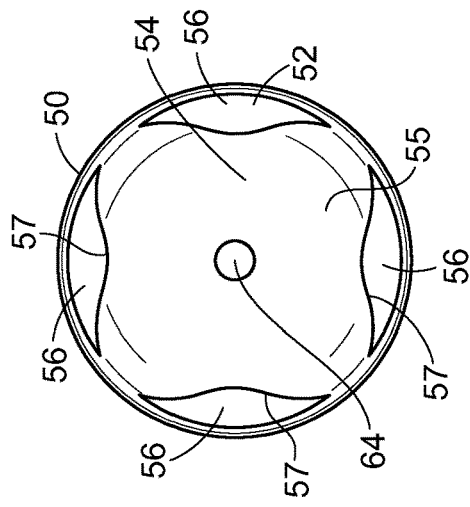
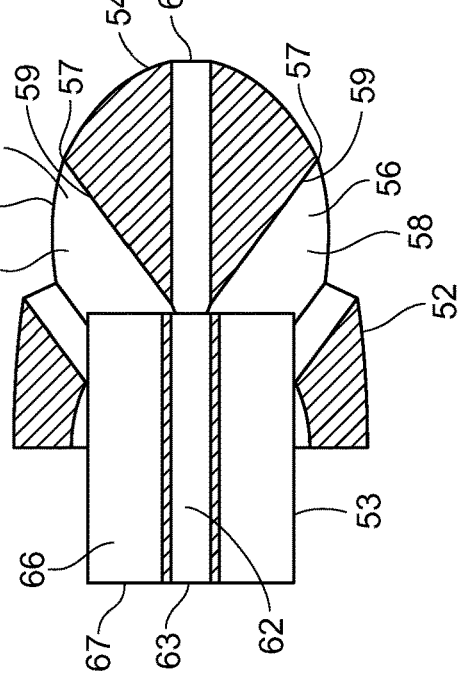

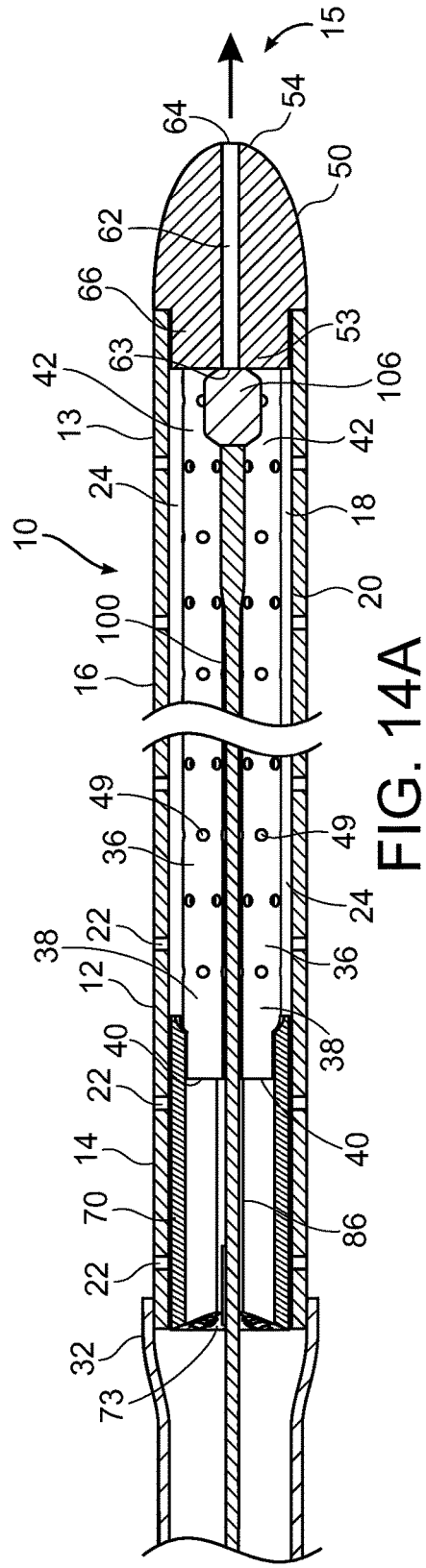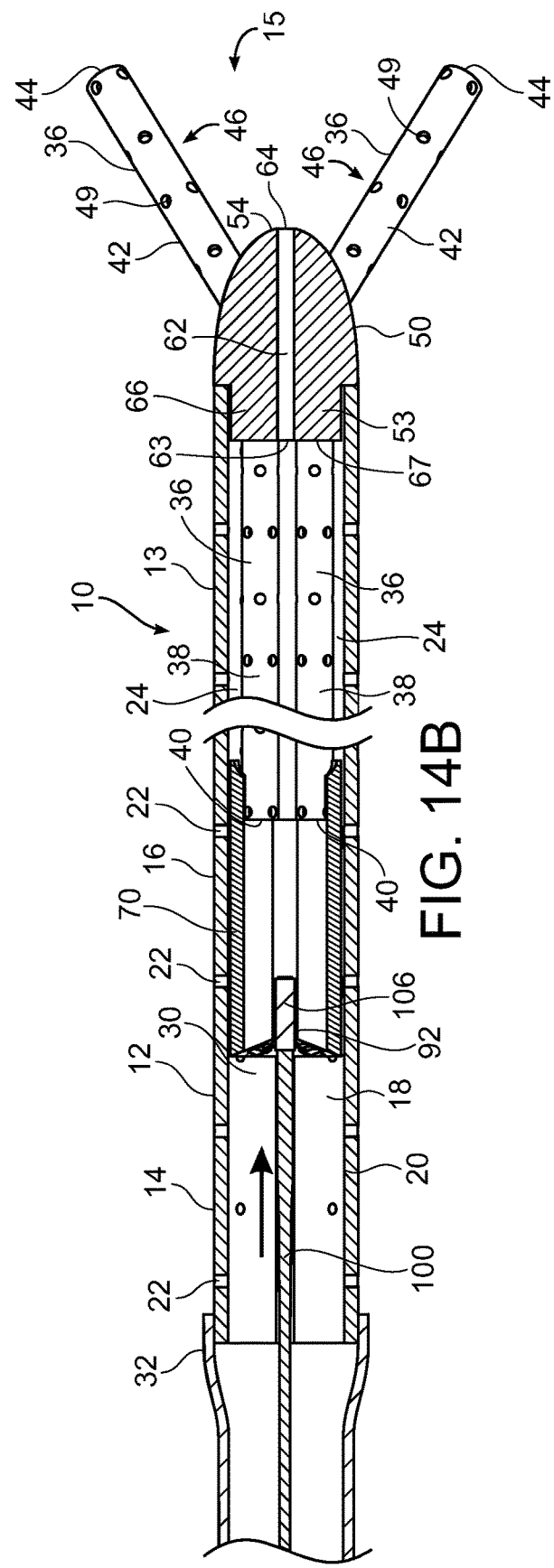
FIG. 14A
FIG. 14B

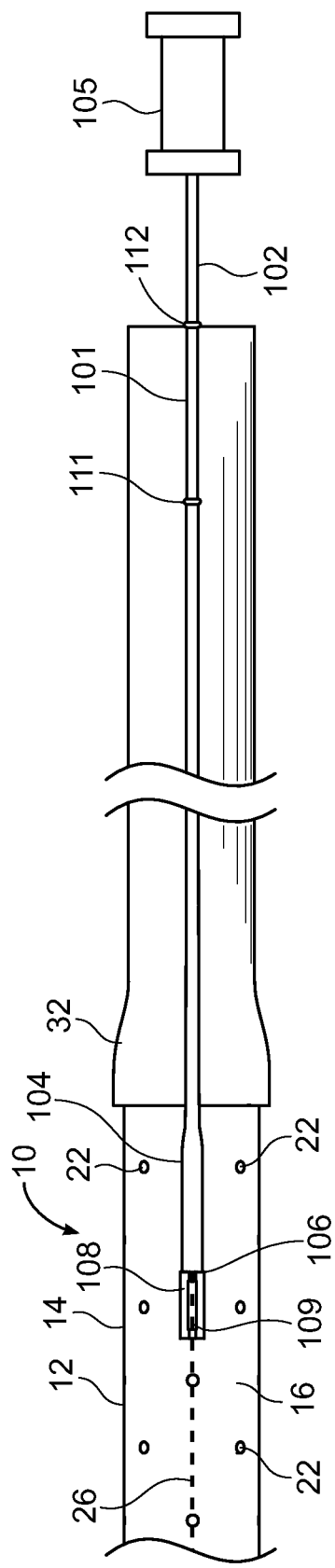
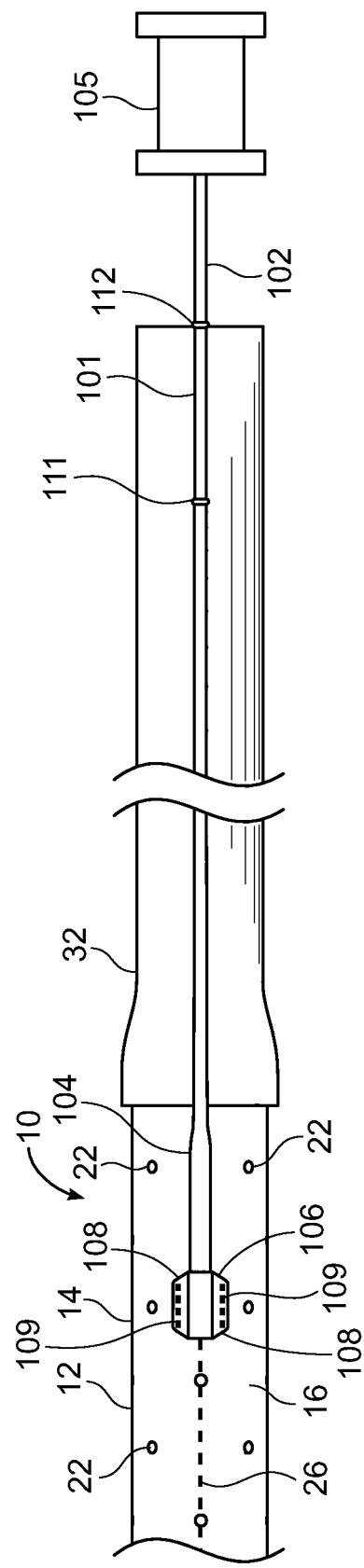

SINGLE LUMEN DRAINAGE CATHETER WITH EXTENDABLE AND RETRACTABLE DRAINS

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND

Field

Example embodiments in general relate to a single lumen drainage catheter with extendable and retractable drains for providing improved fluid drainage and irrigation particularly for medical applications.

Related Art

Any discussion of the related art throughout the specification should in no way be considered as an admission that such related art is widely known or forms part of common general knowledge in the field.

Draining fluid from the body of a subject may be necessary for treating various illnesses. Excessive body fluid can accumulate and cause unwanted symptoms or complications. For example, excess accumulation of cerebrospinal fluid can lead to hydrocephalus, excess accumulation of plural fluid can cause pleural effusion, and excess accumulation of peritoneal fluid can cause ascites. Other fluids that might require drainage include infected fluid in abscesses, blood in hematomas or blood in intravascular catheters.

In other cases, it may be necessary or desirable to artificially introduce fluid into a subject's body from outside to provide irrigation or to washout body wastes. For example, in patients with renal failure peritoneal dialysis is regularly performed by artificially introducing a dialysis fluid from outside a subject's body into the subject's abdomen via a special catheter, and then draining fluid from the subject's body, washing out accumulated wastes and salts in the process.

A common problem facing body fluid drainage catheters is frequent blockage of the catheter. This problem has been addressed using simple procedures such as flushing or manual manipulation. However, such procedures may fail and replacement of the catheter may then become necessary. Catheter replacement can be simple, though uncomfortable, such as in the case of urinary catheter replacement, or it can be complex and require an operative procedure, such as in the cases of cerebrospinal fluid shunt replacement or peritoneal dialysis catheter replacement. In either instance replacement is undesirable and it is preferable to avoid it.

Drainage catheter blockage is frequently attributed to clogged catheter pores or clogged drainage lumens. Typical causes include thick debris in the drained fluid, as in the case of pus drainage, or clotted blood as in the case of hematoma drainage. In other instances, such as when an indwelling catheter is left in situ for a long time, cavity endogenous tissues can coat the catheter's outer surface effectively blocking it from the surrounding fluid to be drained. This condition can arise in connection with peritoneal drainage for example. The tissues of a cavity being drained can even grow inside or through the drainage holes/pores of the catheter. For example, this condition can manifest in connection with a cerebrospinal fluid drainage catheter or when the inflow portion of a ventriculoperitoneal shunt is blocked by the ingrowth of the choroid plexus.

Another challenge with drainage and irrigation catheterization is that in many instances multiple or larger fluid-filled cavities or areas need to be drained or washed at the same time. This can be the case when dealing with multiple abdominal collections or pockets of pus, or after surgery that includes bowel, biliary or urinary tract anastomosis (connection). In other instances, a single cavity or tract may branch into multiple tracts that require drainage simultaneously, such as in the case of the bladder and ureters, the biliary tree, and blood vessels. The traditional approach to drain multiple or larger cavities or areas simultaneously has been to place a separate drainage catheter in each cavity or space through a natural anatomical opening and small incisions, or to use a wider incision to insert multiple catheters.

A number of catheter designs have been proposed in an attempt to address the foregoing problems and challenges. However, the proposed designs have various drawbacks and deficiencies that render them less than desirable from a fluid drainage and irrigation standpoint. For example, some of the proposed designs fail to provide adequate drains and adequate fluid flow pathways and are susceptible to clogging. Additionally, many proposed designs fail to provide the ability to locate tubes in different internal spaces of a subject at the same time and thus fail to provide for multiple spaced apart locations to be drained or irrigated simultaneously.

Some proposed designs attempt to address the problems related to drain and fluid flow paths by providing multiple drains and fluid flow paths. However, many of these designs occupy a relatively large volume of space, which can make insertion in a subject and positioning within the subject difficult and potentially problematic for the subject.

Some proposed designs attempt to address the insertion and positioning problems but require the use of additional tools. Others require additional steps. Both of these additional requirements complicate the insertion process as well as the positioning process within a subject, which may be problematic for the subject. Additionally, many of these designs still fail to provide the very desirable ability to direct multiple tubes to multiple spaced apart internal spaces of a subject to provide drainage or irrigation of such spaces at the same time.

In addition some proposed designs are undesirably complicated to manufacture and to use. This renders such catheters relatively more expensive both in terms of their initial cost and in terms of the additional time and cost that may be associated with procedures in which they are used. Additionally in some cases, the intricate and complex nature of the proposed design may make the catheter more likely to fail during insertion, retraction, or usage, which clearly could be problematic for a subject.

Thus, while a variety of catheter designs have been proposed, the proposed designs have various problems and shortcomings. There remains a need for a catheter that provides increased surface area to enhance drainage rate and reduce the risk of blockage of the catheter drainage ports by fluid debris and/or tissue ingrowth. There also remains a need for such a catheter that can be inserted into a subject percutaneously and through body tissues through a relatively small incision, or through long narrow natural tracts of a subject, such as the digestive and urinary tracts, without causing excessive friction or being prone to obstructions. There further remains a need for such a catheter that can be inserted and positioned within a subject in a plurality of spaced apart locations at the same time to provide simultaneous drainage or irrigation in such locations without the need to separately insert additional catheters. There further remains a need for such a catheter that is relatively simple and inexpensive to manufacture, and that is relatively easy and uncomplicated to use, but that still provides the needed and desirable drainage and irrigation characteristics mentioned above and others.

The example embodiments of a single lumen drainage catheter with extendable and retractable drains disclosed herein are directed to addressing the foregoing needs and the foregoing and other problems and shortcomings of the prior art.

SUMMARY

An example embodiment is directed to a single lumen drainage catheter with extendable and retractable drains. The single lumen drainage catheter with extendable and retractable drains includes a primary catheter that comprises a housing having a distal end portion, a proximal end portion, an exterior, and an interior space that comprises a single unpartitioned lumen. The housing has a common drain that is coupled to the proximal end portion of the housing and that is adapted for a fluid to flow through the common drain. A plurality of drains are arranged within the single unpartitioned lumen with each drain having a proximal end, a distal end, and an interior space between the proximal end and the distal end. Each drain is adapted for the fluid to flow through the interior space between the proximal end and the distal end. The common drain is in fluid communication with the single unpartitioned lumen and with the plurality of drains. The plurality of drains are adapted to be movable within the single unpartitioned lumen between an extended position with at least the distal end portions of the plurality of drains extending to the exterior of the housing and a retracted position with the plurality of drains being enclosed within the single unpartitioned lumen. The plurality of drains in the extended position the plurality of drains provide a first plurality of paths for the fluid to flow between the common drain and the exterior of the housing.

The housing also comprises a first plurality of openings that are adapted for the fluid to flow through between the exterior of the housing and the single unpartitioned lumen. The first plurality of openings provide a second plurality of paths for the fluid to flow between the common drain and the exterior of the housing.

At least one of the drains has a second plurality of openings that are adapted for the fluid to flow between the interior space of the drain and the exterior of the housing when the plurality of drains are in the extended position. The second plurality of openings provide a third plurality of paths for the fluid to flow between the common drain and the exterior of the housing.

The primary catheter also comprises an internal connector that has a proximal end portion, a proximal end surface, a distal end portion, and a distal end surface. The internal connector is enclosed within the single unpartitioned lumen and is selectively movable within the single unpartitioned lumen substantially between the proximal end portion of the housing and the distal end portion of the housing. The plurality of drains are coupled to the internal connector with the proximal ends of the plurality of drains coupled to the distal end portion of the internal connector and the distal end of the drains extending into the single unpartitioned lumen. Movement of the internal connector between the proximal end portion of the housing and the distal end portion of the housing causes the plurality of drains to move between the retracted position and the extended position. Additionally or alternatively one or more elongated tools or other elements can be coupled to the internal connector and caused to move between retracted and extended positions.

The internal connector has a plurality of drain passages that extend through the internal connector and are adapted for the fluid to flow through them. The drain passages are in fluid communication with the plurality of drains and with the common drain so that the fluid can flow through the drain passages between the plurality of drains and the common drain.

An elongated stylet for use with the primary catheter has a proximal end portion and a distal end portion with a specially-shaped distal end tip. The stylet is adapted to be manipulated to insert and move the distal end tip within the single unpartitioned lumen and to cause the distal end tip to selectively engage the internal connector and selectively move the internal connector within the single unpartitioned lumen between a first position at which the plurality of drains (or other tools or elements) are in the retracted position and a second position at which the plurality of drains (or other tools or elements) are in the extended position. The stylet is also adapted to be manipulated to cause the distal end tip to selectively pass through the internal connector and to selectively engage and move the primary catheter.

For that purpose, the internal connector includes a stylet passage, a stylet engagement opening, and a stylet engagement surface. The stylet passage extends through the internal connector between the proximal end surface of the internal connector and the distal end surface of the internal connector and has a first shape and a first orientation. The stylet engagement opening is formed in the proximal end surface of the internal connector and has a second shape and a second orientation. The stylet engagement surface is formed on the distal end surface of the internal connector and has a third shape and a third orientation. The distal end tip of the stylet has a fourth shape and the stylet is adapted to be manipulated to selectively place the distal end tip in the first orientation, the second orientation and the third orientation. The first shape and the fourth shape are configured and adapted so that the distal end tip is able to pass through the stylet passage when the distal end tip is in the first orientation and the distal end tip is not able to pass through the stylet passage when the distal end tip is not in the first orientation. The second shape and the fourth shape are configured and adapted so that the distal end tip is able to enter the stylet engagement opening when the distal end tip is in the second orientation, and the distal end tip is not able to enter the stylet engagement opening when the distal end tip is not in the second orientation. The third shape and the fourth shape are configured and adapted so that the distal end tip is able to engage the stylet engagement surface when the distal end tip is in the third orientation, and the distal end tip is not able to engage the stylet engagement surface when the distal end tip is not in the third orientation. The stylet is adapted to be manipulated to move the internal connector in a direction toward the distal end portion of the housing to place the drains in the extended position when the distal end tip is in the stylet engagement opening, and to move the internal connector in a direction toward the proximal end portion of the housing to place the drains in the retracted position when the distal end tip is engaged with the stylet engagement surface.

There has thus been outlined, rather broadly, some of the embodiments of the drainage catheter with retractable internal drains in order that the detailed description thereof may be better understood, and in order that the present contribution to the art may be better appreciated. There are additional embodiments of the drainage catheter with retractable internal drains that will be described hereinafter and that will form the subject matter of the claims appended hereto. In this respect, before explaining at least one embodiment of the drainage catheter with retractable internal drains in detail, it is to be understood that the drainage catheter with retractable internal drains is not limited in its application to the details of construction or to the arrangements of the components set forth in the following description or illustrated in the drawings. The drainage catheter with retractable internal drains is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 1 is a perspective view of a single lumen drainage catheter with extendable and retractable drains with the drains retracted in accordance with an example embodiment.

FIG. 2 is a perspective view of a single lumen drainage catheter with extendable and retractable drains with the drains extended in accordance with an example embodiment.

FIG. 3 is a side view of a single lumen drainage catheter with extendable and retractable drains with the drains retracted in accordance with an example embodiment.

FIG. 4 is a side view of a single lumen drainage catheter with extendable and retractable drains with the drains extended in accordance with an example embodiment.

FIG. 7A is a cross-sectional side view of a single lumen drainage catheter with extendable and retractable drains with the drains retracted in accordance with an example embodiment.

FIG. 7B is a cross-sectional side view of a single lumen drainage catheter with extendable and retractable drains with the drains extended in accordance with an example embodiment.

FIG. 8A is a partially transparent perspective view of a single lumen drainage catheter with extendable and retractable drains with the drains retracted in accordance with an example embodiment.

FIG. 8B is a cross-sectional distal end portion view taken along section line 8B-8B of FIG. 8A of a single lumen drainage catheter with extendable and retractable drains with the drains retracted in accordance with an example embodiment.

FIG. 8C is a cross-sectional distal end portion view taken along section line 8C-8C of FIG. 8A of a single lumen drainage catheter with extendable and retractable drains with the drains retracted in accordance with an example embodiment.

FIG. 9A is a perspective view of a distal end cap of a single lumen drainage catheter with extendable and retractable drains in accordance with an example embodiment.

FIG. 9B is a side view of a distal end cap of a single lumen drainage catheter with extendable and retractable drains in accordance with an example embodiment.

FIG. 9C is a cross-sectional side view of a distal end cap of a single lumen drainage catheter with extendable and retractable drains in accordance with an example embodiment.

FIG. 9D is a distal end portion view of a distal end cap of a drainage catheter with extendable and retractable drains in accordance with an example embodiment.

FIG. 9E is a proximal end portion view of a distal end cap of a single lumen drainage catheter with extendable and retractable drains in accordance with an example embodiment.

13A illustrating the distal end tip of the stylet advanced in a distal direction through the pass-slot of the internal connector in accordance with an example embodiment.

Figure 13A:
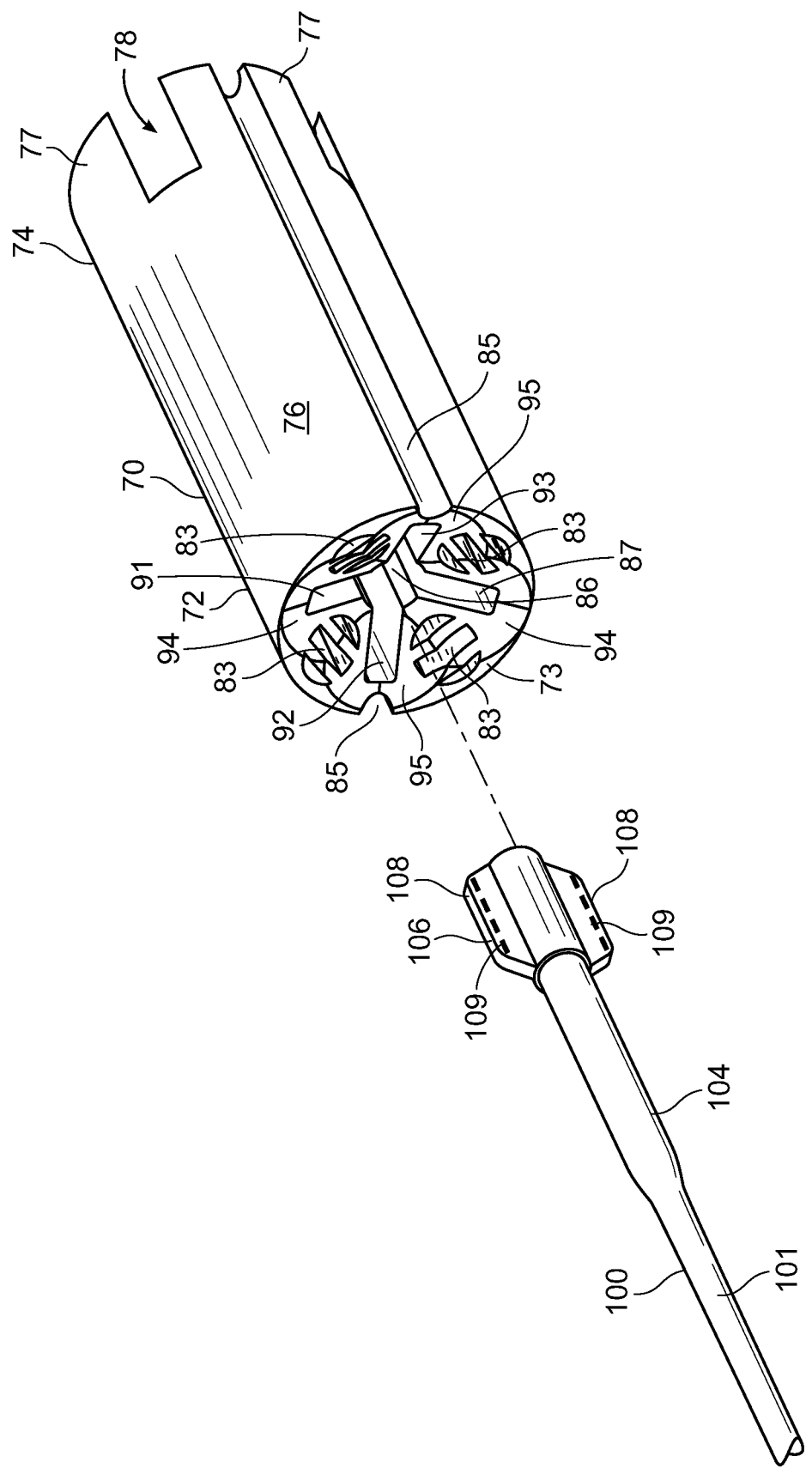
FIG. 13A is a perspective view of an internal connector of a single lumen drainage catheter with extendable and retractable drains and a portion of a stylet for use with the catheter illustrating a distal end tip of the stylet aligned with a pass-slot on a proximal end portion of the internal connector in accordance with an example embodiment.
Figure 13B:
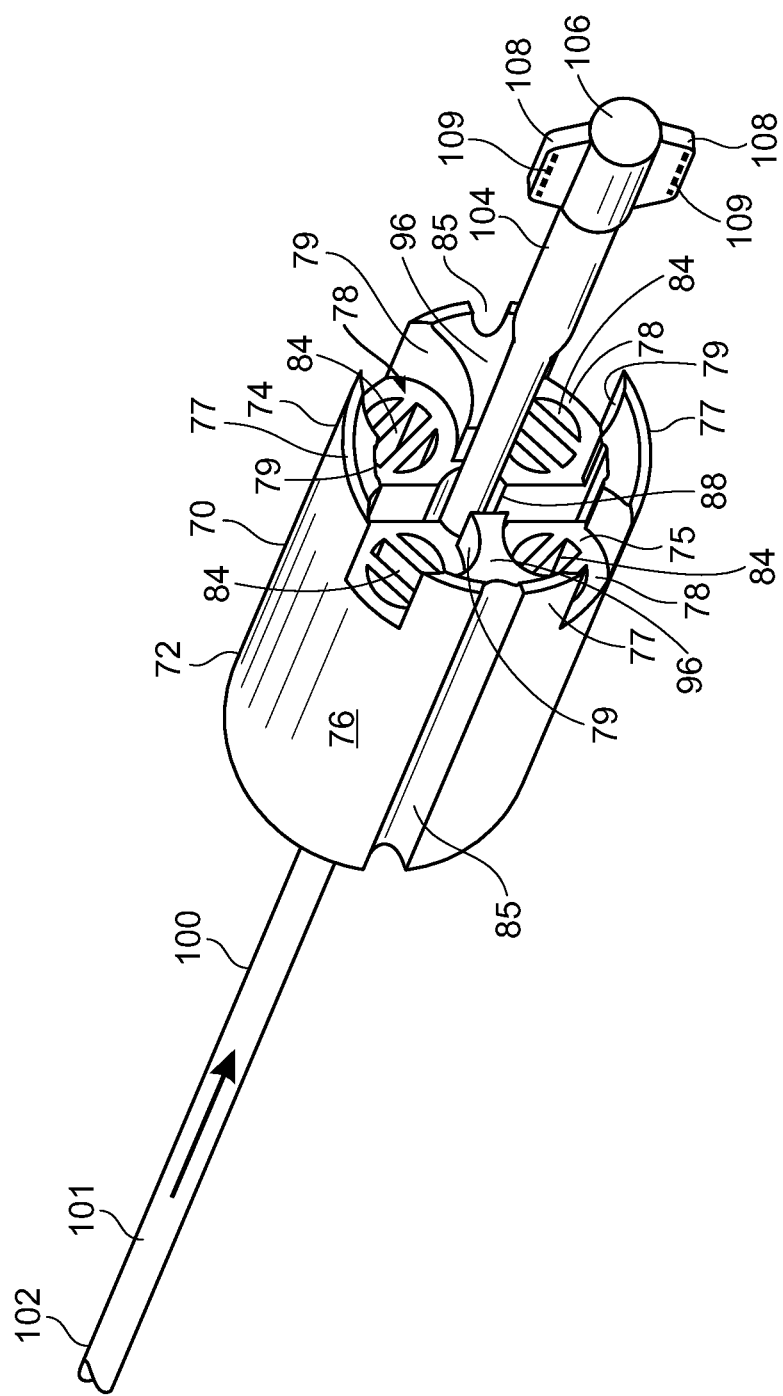
FIG. 13B is perspective view of the internal connector of the single lumen drainage catheter with extendable and retractable drains and the portion of the stylet shown in FIG.
Figure 13C:
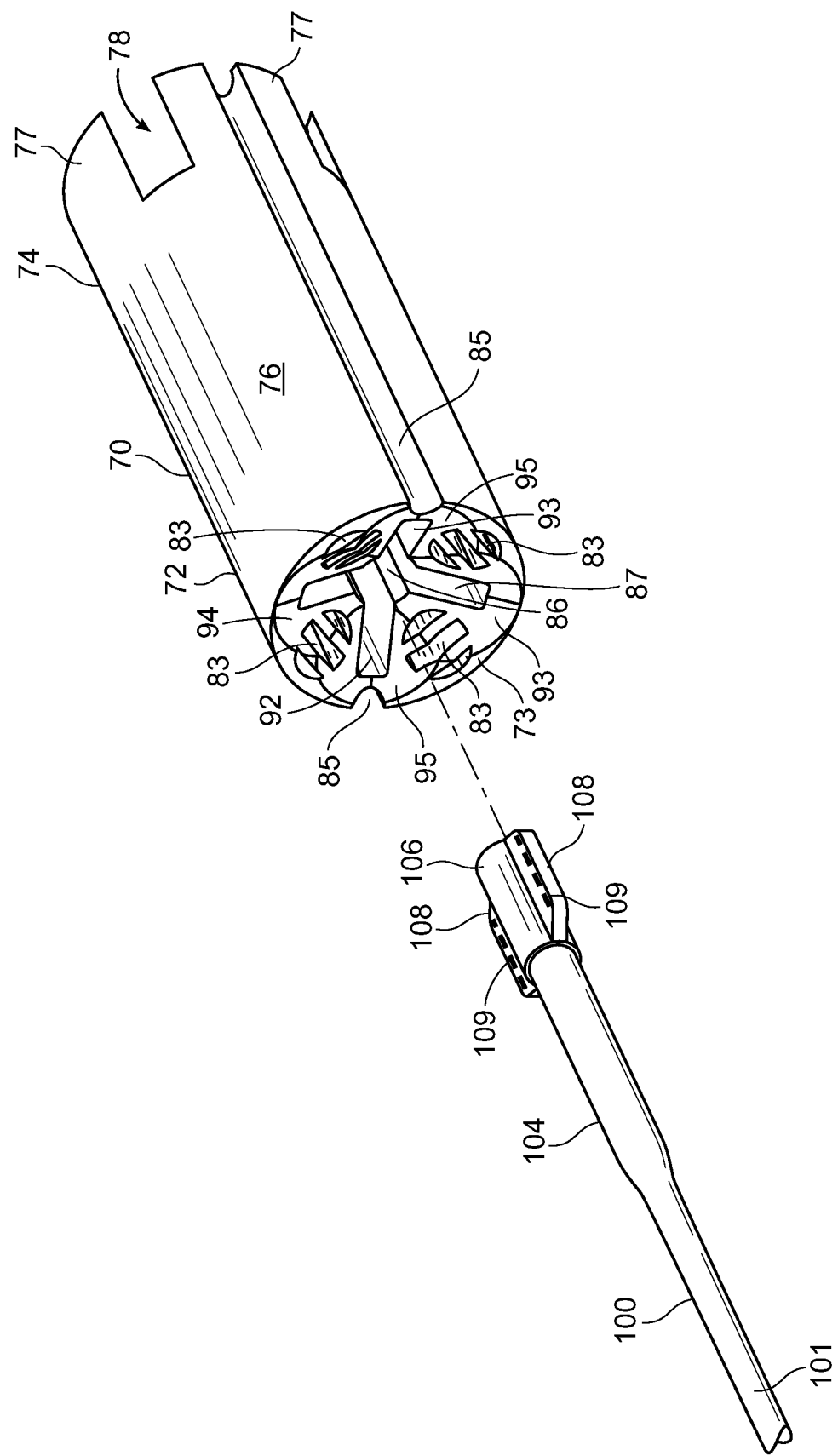

FIG. 13C is a perspective view of an internal connector of a single lumen drainage catheter with extendable and retractable drains and a portion of a stylet for use with the catheter illustrating a distal end tip of the stylet aligned with a stop-slot on a proximal end portion of the internal connector in accordance with an example embodiment.

Figure 13D:
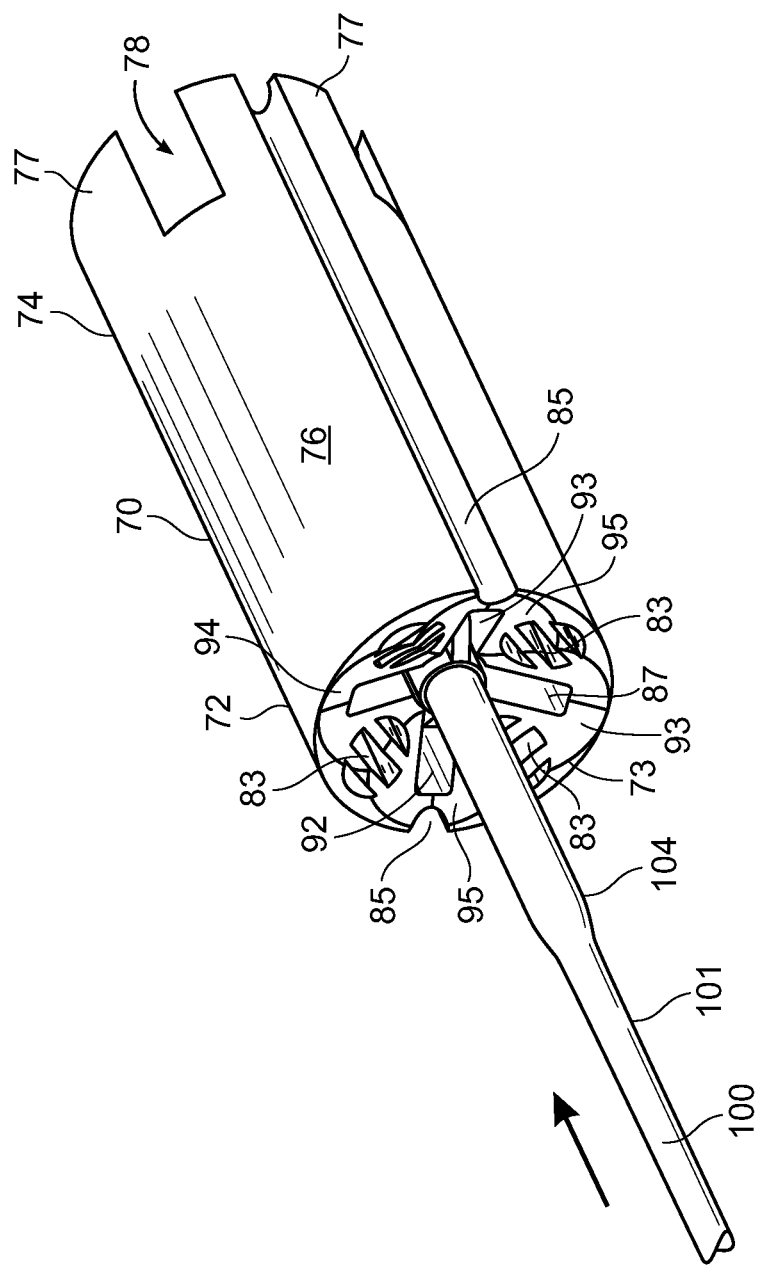

FIG. 13D is perspective view of the internal connector of the single lumen drainage catheter with extendable and retractable drains and the portion of the stylet as shown in FIG. 13C illustrating the distal end tip of the stylet in engagement with the stop-slot of the internal connector in accordance with an example embodiment.

Figure 13E:
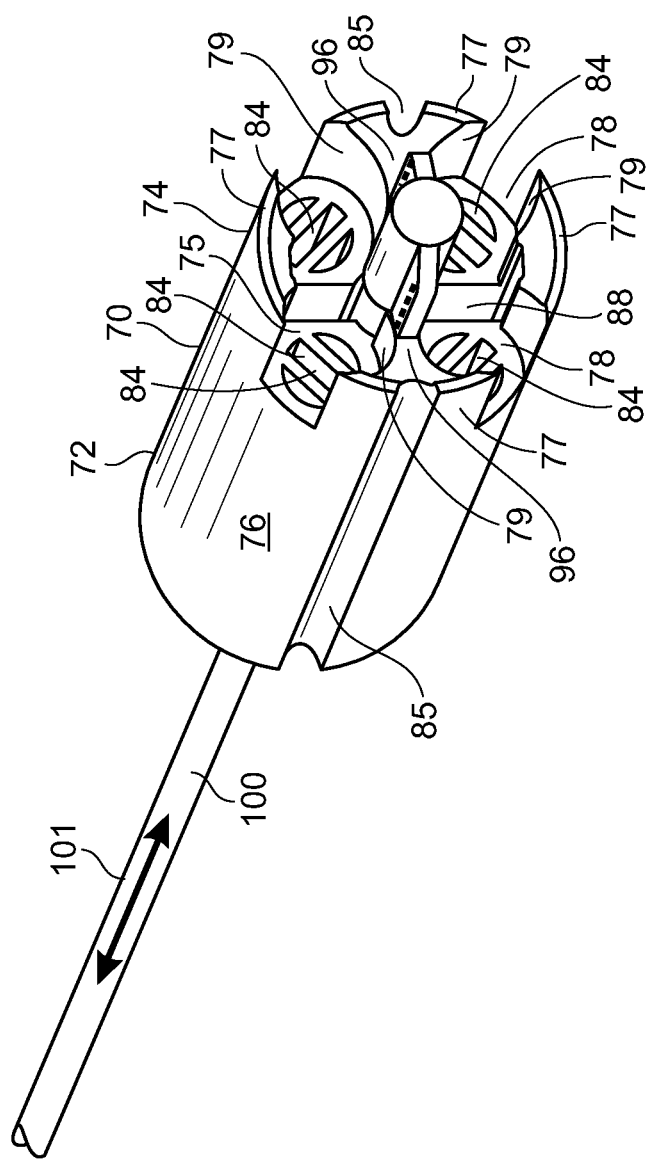

FIG. 13E is a perspective view of the internal connector of the single lumen drainage catheter with extendable and retractable drains and the portion of the stylet as shown in FIGS. 13B-13C illustrating the distal end tip of the stylet in engagement with a distal side of the internal connector for moving the internal connector in a proximal direction in accordance with an example embodiment.

FIG. 14A is a cross-sectional top view of a single lumen drainage catheter with extendable and retractable drains and a stylet for use with the catheter illustrating the stylet inserted in the catheter with a distal end tip of with the stylet in engagement with the distal end cap of the catheter and the catheter being advanced in a distal direction in accordance with an example embodiment.

FIG. 14B is a cross-sectional top view of a single lumen drainage catheter with extendable and retractable drains and a stylet for use with the catheter illustrating the stylet inserted in the catheter with a distal end tip in engagement with an internal connector of the catheter and the internal connector being advanced in a distal direction to extend drain tubes of the catheter in accordance with an example embodiment.

Figure 14C:
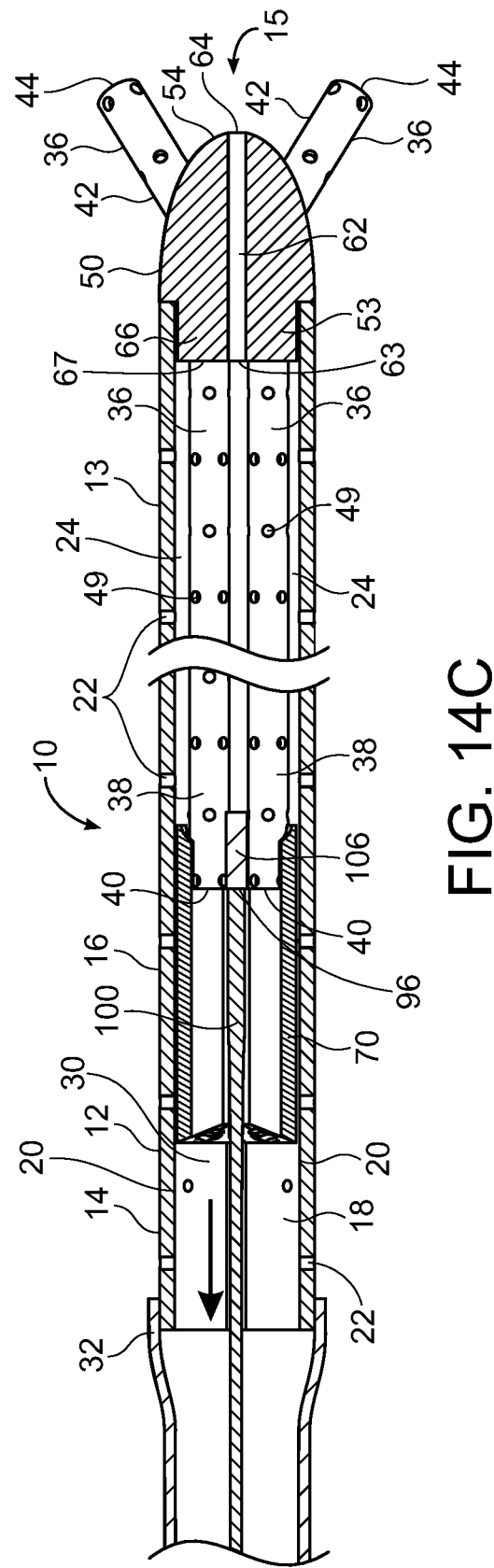

FIG. 14C is a cross-sectional top view of a single lumen drainage catheter with extendable and retractable drains and a stylet for use with the catheter illustrating the stylet inserted in the catheter with a distal end tip of the stylet in engagement with an internal connector of the catheter and the internal connector being retracted in a proximal direction to retract drain tubes of the catheter in accordance with an example embodiment.

FIG. 15A is a partial transparent top view of a single lumen drainage catheter with extendable and retractable drains and a stylet for use with the catheter illustrating an orientation of alignment markers on an outer housing of the catheter and on a distal end tip of the stylet when the distal end tip is oriented in a first alignment with an internal connector of the catheter in accordance with an example embodiment.

FIG. 15B is a partial transparent top view of a single lumen drainage catheter with extendable and retractable drains and a stylet for use with the catheter illustrating an orientation of alignment markers on an outer housing of the drainage catheter and on a distal end tip of the stylet when the distal end tip is oriented in a second alignment with an internal connector of the catheter in accordance with an example embodiment.

Figure 16:
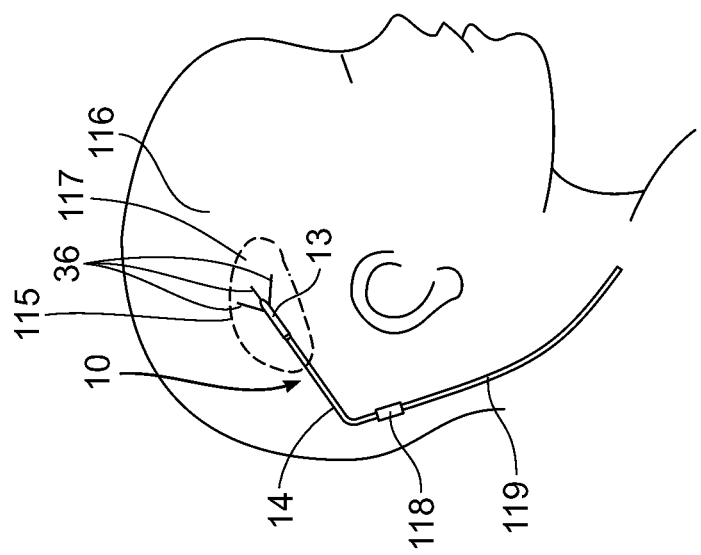

FIG. 16 is a partial side cutaway view of a single lumen drainage catheter with extendable and retractable drains in accordance with an example embodiment implanted within a ventricle of a subject and integrated with a ventriculoperitoneal shunt system.

Figure 17:
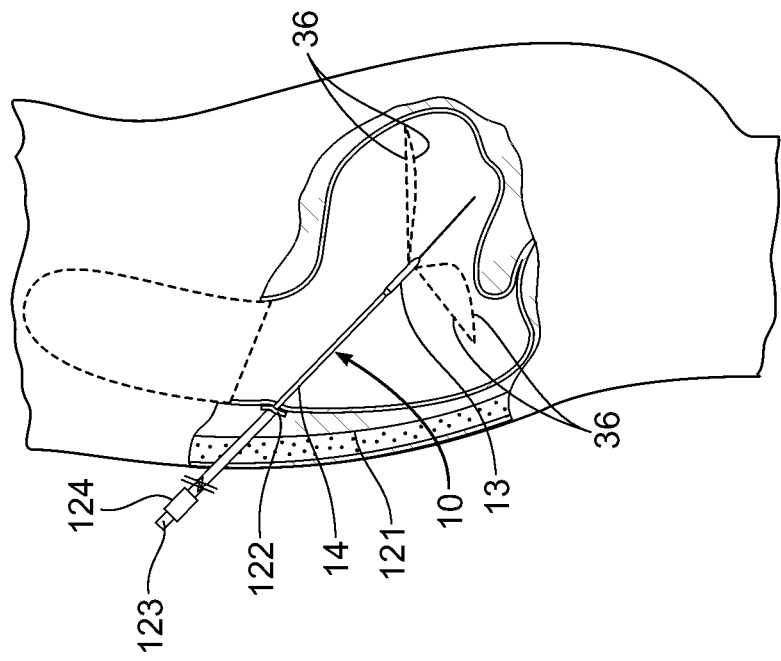

FIG. 17 is a partial side cutaway view of a single lumen drainage catheter with extendable and retractable drains in accordance with an example embodiment implanted within a peritoneal cavity of a subject and integrated with a peritoneal dialysis system.

DETAILED DESCRIPTION

A. Overview.

With reference to the drawings, an example single lumen drainage catheter with extendable and retractable drains generally comprises a primary catheter 10 and a plurality of drains 36. The primary catheter 10 comprises a housing 12, a common drain 32, an end cap 50, and an internal connector 70. The housing 12 is elongated and has a longitudinal axis, a proximal end portion 14, a distal end portion 13, and an interior space 18 that comprises a single unpartitioned lumen 30. The housing 12 has a plurality of spaced apart openings 22 between the distal end portion 13 and the proximal end portion 14 which provide a plurality of paths through which fluid can flow between the interior space 18 and the exterior 15 of the housing 12.

The common drain 32 is coupled to the proximal end portion 14 of the housing 12 and is in fluid communication with the single lumen 30 and with the plurality of drains 36. Fluid is thus able to flow between the common drain 32 and the exterior 15 of the primary catheter housing 12 through a plurality of pathways.

Each of the plurality of drains 36 comprises an elongated tube with a distal end portion 42, distal end portion opening 44, proximal end portion 38, proximal end portion opening 40, and an interior space 48 through which fluid can flow between the openings. Alternatively, the distal end opening 44 may be omitted and the distal end can be closed. Each tube also has a plurality of openings 49 along the tube between the distal and proximal end portions which provide a plurality of paths through which fluid can flow between the interior space 48 and the exterior 46 of the tube. The plurality of drains 36 are movable within the single lumen 30 between an extended position in which at least the distal end portions 42 of the drains 36 extend to the exterior 15 of the housing 12 and a retracted position in which the drains 36 are enclosed within the single lumen 30. The drains 36 thus provide a plurality of paths for fluid to flow between the exterior 15 of the primary catheter housing 12 and the common drain 32.

The end cap 50 is coupled to the distal end portion 13 of the housing 12 and includes a plurality of spaced apart drain ports 56 and guides 58. The drain ports 56 extend between the interior space 18 and the exterior 15 of the housing 12 and are adapted for the plurality of drains 36 to pass through as the drains 36 are moved between the retracted and extended positions. As the drains 36 are moved to the extended position, the guides 58 guide the drains 36 through the drain ports 56 at angles relative to the primary catheter housing 12 to provide for drainage and irrigation over an expanded area.

The internal connector 70 is enclosed within the single lumen 30 and has a proximal end portion 72, a proximal end surface 73, a distal end portion 74, and a distal end surface 75. The proximal end portions 38 of the plurality of drains 36 are removably coupled to the distal end portion 74 of the internal connector 70 by a plurality of holding bars 77 with the distal end portions 42 of the drains 36 extending into the single lumen 30 toward the distal end portion 13 of the housing 12. Additionally or alternatively one or more elongated tools or other elements can be removably coupled to the internal connector 70 by the holding bars 77. A plurality of drain passages 82 extend through the internal connector 70 and provide a plurality of paths for fluid to flow between the drains 36 and the common drain 32. The internal connector 70 also comprises a stylet passage 86 that extends through the internal connector 70, a stylet engagement opening 92 in the proximal end surface 73, and a stylet engagement surface 96 on the distal end surface 75.

An elongated stylet 100 is designed to be used with the primary catheter 10. The stylet 100 has an elongated shaft 101 connecting a proximal end portion 102 and a distal end portion 104 with a specially-shaped distal end tip 106. The distal end tip 106 and the internal connector 70 are configured and adapted so that the stylet 100 can be manipulated to cause the distal end tip 106 to selectively pass through the internal connector 70 or to selectively engage the internal connector 70. When the distal end tip 106 is passed through the internal connector 70, the stylet 100 can be manipulated to selectively move the primary catheter 10, for insertion or positioning in a subject for example. When the internal connector 70 is engaged by the distal end tip 106, the stylet 100 can be manipulated to selectively move the internal connector 70 within the single lumen 30 of the housing 12 between the proximal end portion 14 and distal end portion 13 of the housing 12 to cause the plurality of drains 36 and/or other tools or elements to move between the retracted and extended positions.

The stylet passage 86 of the internal connector 70 enables the distal end tip 106 of the stylet 100 to selectively pass through the internal connector 70 when the distal end tip 106 is in a first orientation aligned with the stylet passage 86. The stylet engagement opening 92 of the internal connector 70 is adapted to receive and be entered by the distal end tip 106 in engagement with the internal connector 70 when the distal end tip 106 is in a second orientation aligned with the stylet engagement opening 92. With the distal end tip 106 in the stylet engagement opening 92, the stylet 100 can be manipulated to move the internal connector 70 to a second position in the single lumen 30 to place the drains 36 in the extended position. The stylet engagement surface 96 is adapted to be engaged by the distal end tip 106 when the distal end tip 106 is in a third orientation aligned with the stylet engagement surface 96. With the distal end tip 106 in engagement with the stylet engagement surface 96, the stylet 100 can be manipulated to move the internal connector 70 to a first position in the single lumen 30 to place the drains 36 in the retracted position.

The example drainage catheter with retractable internal drains thus provides for selectively extending and retracting a plurality of drains from a primary catheter to provide a plurality of paths for fluid to flow between a relatively large area exterior to the primary catheter and a common drain and thus provides substantially improved drainage and irrigation.

B. Housing.

With reference to the drawings, and particularly FIGS. 1-4, 7A-7B, 12A-12B, and 14A-14C, the example drainage catheter with retractable internal drains comprises a primary catheter 10 with an elongated housing 12 having a longitudinal axis. The housing 12 has a distal end portion 13, a proximal end portion 14, an exterior 15, an exterior surface 16, an interior space 18, and an interior surface 20. The interior space 18 and the interior surface 20 preferably extend substantially the entire distance between the distal end portion 13 and the proximal end portion 14 of the housing 12.

The housing 12 preferably has a plurality of relatively small openings 22 formed in the exterior surface 16 of the housing 12 that extend through the housing 12 into the interior space 18. The openings 22 are preferably spaced apart along the exterior surface 16 of the housing 12 at least part of the way and preferably substantially the entire distance between the distal end portion 13 of the housing 12 and the proximal end portion 14 of the housing 12. The openings 22 are dimensioned and configured to allow fluid to flow through the openings 22 between the exterior 15 of the housing 12 and the interior space 18 of the housing 12. The plurality of openings 22 thus provide a plurality of paths for the fluid to flow between the exterior 15 of the housing 12 and the common drain 32 which is described further below.

The housing 12 preferably also comprises an engagement element 24 on the interior surface 20 of the housing 12. The engagement element 24 is configured and adapted to be in movable engagement with a corresponding engagement element 85 of the internal connector 70, which is described further below, as the internal connector 70 moves within the interior space 20 of the housing 12 between the proximal end portion 14 and the distal end portion 13 of the housing 12. The engagement element 24 and the corresponding engagement element 85 are configured and adapted to mutually engage so as to maintain a fixed angular alignment between the internal connector 70 and the housing 12 and to prevent the internal connector 70 from rotating within the housing 12 as the internal connector 70 moves within the interior space 20 of the housing 12 between the distal end portion 13 and the proximal end portion 14 of the housing 12.

The engagement element 24 may comprise one element or a plurality of elements spaced about the interior surface 20. For example two elements could be spaced apart opposite each other on opposite sides of the interior surface 20. Preferably, the engagement element 24 will extend longitudinally along the interior surface 20 of the housing 12 between the proximal end portion 14 and the distal end portion 13 of the housing 12. Also preferably, the engagement element 24 will extend for a distance sufficient to maintain the angular alignment between the internal connector 70 and the housing 12 along the entire or substantially the entire length of travel of the internal connector 70 within the housing 12 as the internal connector 70 moves between a first position in which the plurality of drains 36 are in a retracted position and a second position in which the plurality of drains 36 are in an extended position, as further described below. The engagement structure 24 thus may comprise a protrusion such as an elongated rib as seen for example in FIGS. 7B, BA, and 8C for example. Alternatively, the engagement structure 24 may comprise an indent such as an elongated groove, and may also comprise a protrusion or indent having a variety of shapes suitable for the stated purpose.

The housing 12 may also include an alignment marker 26. The alignment marker 26 is configured and adapted to align the stylet 100 with the housing 12 so as to allow the stylet 100 to be remotely manipulated to selectively pass through or to engage the internal connector 70 within the housing 12 as described further below. More specifically, the alignment marker 26 is configured and adapted to be aligned with corresponding alignment markers 109 on the distal end tip 106 of the stylet 100 in a first alignment in which the distal end tip 106 is in a first orientation aligned with a stylet passage 86 of the internal connector 70 and able to pass through the internal connector 70, and in a second alignment in which the distal end tip 106 is in a second orientation aligned with a stylet engagement opening 92 and/or a stylet engagement surface 96 of the internal connector 70 and able to engage the internal connector 70 and move it within the interior space 20 of the housing 12 between the distal end portion 13 and the proximal end portion 14 of the housing 12.

The alignment marker 26 may comprise a single marker or a plurality or set of markers as seen in FIGS. 15A and 15B for example. Preferably the alignment marker 26 extends longitudinally along the exterior surface 16 of the housing 12 between the proximal end portion 14 and the distal end portion 13 of the housing 12. The alignment marker 26 may extend for part of or up to substantially the entire distance the internal connector 70 is able to move within the housing 12.

The alignment marker 26 is adapted to provide a remote visual indication of alignment. Preferably the alignment marker 26 comprises a material or substance that is substantially radio-opaque. This enables the alignment marker 26 to provide a remote visual indication of alignment when the primary catheter 10 is within a subject and being remotely positioned under the visual guidance provided by radio-imaging equipment.

The housing 12 may be but is not necessarily formed as an elongated cylinder with a longitudinal axis. The interior space 18 of the housing 12 also may but need not necessarily comprise an elongated cylindrical space. It will be appreciated that other shapes may also be used for the housing 12 and the interior space 18 depending on the needs of a particular intended application. However, forming the housing 12 as an elongated structure with a relatively small diameter is preferred to facilitate insertion and location of the primary catheter 10 within a subject. It will be appreciated that the housing 12 and the interior space 18 may be constructed with various length and diameter dimensions depending on the intended application, the anatomy of a subject to be catheterized, the desired drainage and irrigation performance, and other considerations. The housing 12 is ideally formed of a flexible material such as polyurethane or medical silicon, but other materials suitable for use in catheter applications also may be used.

C. Single Lumen.

The interior space 18 of the housing 12 comprises a single lumen 30. The single lumen 30 is unpartitioned and preferably extends substantially the entire distance between the proximal end portion 14 and the distal end portion 13 of the housing 12. More specifically, the single lumen 30 extends substantially from the common drain 32 of the housing 12 to the end cap 50 of the housing 12, both of which are described further below.

The single lumen 30 is preferably unpartitioned over its entire length. By unpartitioned it is meant that no partitions, tracks, or other physical structures physically subdivide or interrupt the interior space 18 comprising the single lumen 30 within which the engagement element 24, described above, and the plurality of drains 36 and the internal connector 70, described below, are located. Thus, the plurality of drains 36 are positioned within and allowed to move within the single lumen 30, as described further below, free from physical engagement with any structures, other than the internal connector 70 and the interior surface 20 of the housing 12, until the drains 36 reach the end cap 50 of the housing 12. Because the single lumen 30 is unpartitioned, the primary catheter 10 is simpler and less expensive to manufacture. In addition, substantially the full volume of the interior space 18 of the housing 12 is maintained, which provides improved flow for drainage and irrigation fluids.

In an embodiment wherein the housing 12 is in the form of an elongated cylinder with a longitudinal axis, the space comprising the single lumen 30 also may be substantially cylindrical and may be axially symmetrical with respect to the longitudinal axis of the housing 12.

D. Common Drain.

The primary catheter 10 comprises a common drain 32. The common drain 32 is fluidly coupled to the proximal end portion 14 of the housing 12. The coupling between the common drain 32 and the housing 12 preferably comprises a substantially fluid-tight connection. The common drain 32 also preferably includes one or more connections or fittings suitable to fluidly couple the common drain 32 and hence the primary catheter 10 to a source of irrigation fluid or to a drainage fluid reservoir, container, or drain directly or via one or more tubes, conduits, and/or other suitable plumbing elements.

The common drain 32 is in fluid communication with the single lumen 30 of the interior space 18 of the housing 12 and with the plurality of drains 36. The common drain 32 is adapted for fluid to flow through the common drain 32 between the source of irrigation fluid, drainage fluid reservoir, or the like, and the single lumen 30 and drains 36. The common drain 32 is also adapted for fluid to flow between the source of irrigation fluid, drainage fluid reservoir, or the like and the exterior 15 of the housing 12 through the drains 36, a plurality of openings 49 in the drains 36, which are described below, and the plurality of openings 22 in the housing 12. Accordingly, the primary catheter 10 provides a plurality of paths for fluid to flow between the common drain 32 and the exterior 15 of the housing 12 to provide improved drainage and irrigation.

In an embodiment wherein the housing 12 is in the form of an elongated cylinder with a longitudinal axis, the common drain 32 may be aligned with the space comprising the single lumen 30 substantially along the longitudinal axis of the housing 12.

E. Extendable and Retractable Drains.

Figure 5:
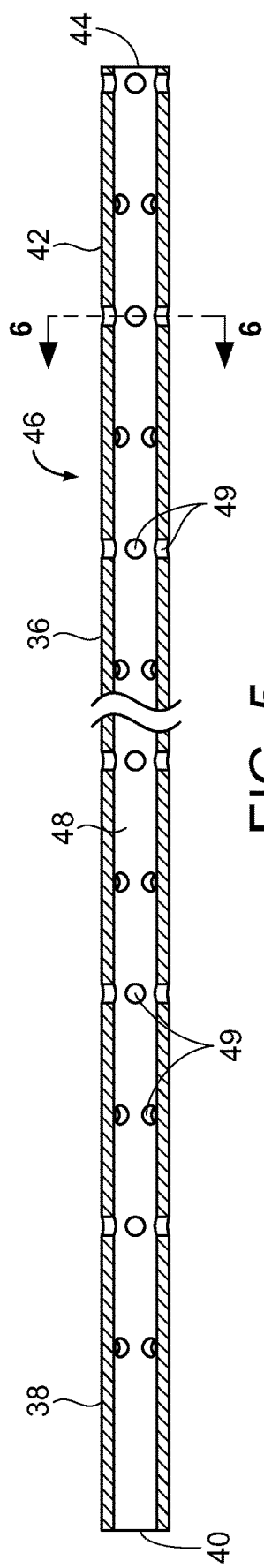
FIG. 5 is a side view of a retractable internal drain of a single lumen drainage catheter with extendable and retractable drains in accordance with an example embodiment.
Figure 6:
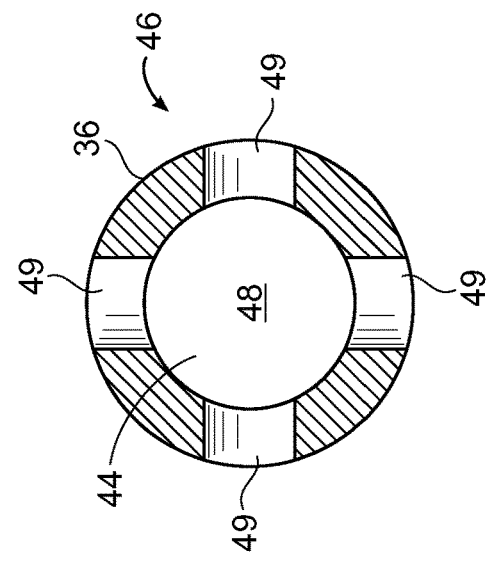
FIG. 6 is a cross-sectional end view taken along section line 6-6 of FIG. 5 of an extendable and retractable drain of a single lumen drainage catheter with extendable and retractable drains in accordance with an example embodiment.

With reference to the drawings, and particularly FIGS. 2, 4-6, 7A-7B, 8A-8C, 12A-12B, and 14A-14C, the example drainage catheter with retractable internal drains comprises a plurality of elongated drains 36. As shown specifically in FIGS. 5-6, each drain 36 has a proximal end portion 38, a proximal end portion opening 40, a distal end portion 42, a distal end portion opening 44, an exterior 46, and an interior space 48. The interior space 48 extends between the proximal end portion opening 40 and the distal end portion opening 44. Each drain 36 is adapted for fluid to flow between the exterior 46 of the drain 36 and the interior space 48 of the drain 36 through the proximal end portion opening 40 and distal end portion opening 42, and for fluid to flow between the proximal end portion opening 40 and the distal end portion opening of the drain 36 through the interior space 48.

Preferably at least one of the drains 36 and more preferably each of the plurality of drains 36 comprises an elongated linear hollow tube that is substantially cylindrical in shape. However, it will be appreciated that, depending on the intended application, the drains 36 can be formed in various shapes including a linear, curved, or coiled shape, such as a helix. It will be appreciated that a coil-shaped tube can provide more overall tube length and thus drainage area when the drains 36 are in the extended position compared to a straight tube while still being able to be fully enclosed within the same length of housing 12 when the drains 36 are in the retracted position enclosed within the single lumen 30.

The drains 36 can be selected to have length within a range depending on the intended application and needs. However, the overall lengths of the drains 36 should be selected so that when the drains 36 are in the retracted position they are fully enclosed within the single lumen 30 in the interior space 18 of the housing 12 as illustrated in FIGS. 1, 7A, 8A, 12A, and 14A for example. It will also be appreciated that while it is preferred that all of the drains 36 have the same shape and dimensions, it is not necessary that all of the drains 36 be of the same shape or have the same dimensions.

Preferably at least one of the drains 36 and more preferably each of the plurality of drains 36 has a second plurality of small openings 49 or perforations that extend through the drain 36 from the exterior 46 of the drain 36 to the interior space 48 of the drain 36. The openings 49 or perforations are preferably spaced apart along the drain 36 at least part of the way and preferably substantially the entire distance between the distal end portion 42 and the proximal end portion 38 of the drain 36. The openings 49 are dimensioned and adapted to allow fluid to flow through the openings 49 between the exterior 46 of the drain 36 and the interior space 48 of the drain 36. The plurality of openings 49 thus provide a plurality of paths for the fluid to flow between the exterior 46 and the interior space 48 of the drain 36 in addition to the path through the interior space 48 between the proximal end portion opening 40 and the distal end portion opening 44.

Thus, when the plurality of drains 36 extend to the exterior 15 of the housing 12 in the extended position, each drain 36 and the plurality of drains 36 are adapted to provide a plurality of paths for fluid to flow between the interior space 48 of each drain 36, the interior space 18 of the housing 15, and the exterior 15 of the housing 12. Further, because the drains 36 are in fluid communication with the common drain 32, as described herein, the drains 36 provide a plurality of paths for the fluid to flow between the common drain 32 and the exterior 15 of the housing 12.

The drains 36 preferably are formed of polyurethane or silicon and are relatively flexible. This flexibility minimizes the potential for the drains 36 to cause damage to surrounding tissues of a subject when the drains 36 are moved into the extended position. However, it is understood that any number of other materials may also be used consistent with the intended function of the drains 36 as described herein and the intended applications of the primary catheter 10.

The plurality of drains 36 are arranged so that when they are enclosed within the single lumen 30, they extend longitudinally within the lumen 30 between the proximal end portion 14 and the distal end portion 13 of the housing 12. As will be described further below, the plurality of drains 36 are coupled to the internal connector 70 with the proximal end portions 38 of the drains 36 being coupled to a distal end portion 75 of the internal connector 70. The distal end portions 42 of the drains 36 extend into the single lumen 30 in a direction toward the distal end portion 13 of the housing 12 and into proximity with the end cap 50.

The plurality of drains 36 are adapted to be movable within the single lumen 30 between an extended position (FIGS. 2, 4, 7B) and a retracted position (FIGS. 1, 3, 7A, 8A, 12A). FIG. 14B shows the drains 36 being moved in the direction of the distal end portion 13 of the housing 12 and in transition from the retracted position to the extended position. FIG. 14C shows the drains 36 being moved in the direction of the proximal end portion 14 of the housing 12 and in transition from the extended position to the retracted position. The drains 36 are movable within and relative to the single lumen 30 in the interior space 18 of the housing 12 without engagement with partitions, guides, tracks or other physical structures to maintain or direct the positions of the drains 36 within the single lumen 30.

In the extended position, at least the distal end portions 42 of the plurality of drains 36 extend to the exterior 15 of the housing 12 through drain ports 56 of the end cap 50, which is described below. Thus, in the extended position the plurality of drains 36 provide a plurality of paths for fluid to flow between the exterior 15 of the housing 12 and the common drain 32. In the retracted position, the plurality of drains 36 are enclosed within the single lumen 30 in the interior space 18 of the housing 12.

In the example embodiments, it is contemplated that the plurality of drains 36 are movable together as a single group between the retracted position and the extended position and that all of the drains 36 will have the same length and thus reach the extended position together and at the same time. However, it will be appreciated that the drains 36 could have different length dimensions. In that case, as the drains 36 are moved to the extended position a first drain or first plurality of drains 36 could be brought to the extended position prior to a second drain or second plurality of drains 36 reaching the extended position, and further movement of the drains 36 in the direction of the distal end portion 13 of the housing 12 could be required to bring the second drain or second plurality of drains 36 to the extended position. Thus, the drains 36 could be arranged such that there are two or even more drains or pluralities of drains 36 with two or more extended positions and a drain or drains 36 could be brought to and reach the extended position sequentially and at different times.

F. End Cap.

The primary catheter 10 comprises an end cap 50. The end cap 50, details of which are illustrated in FIGS. 9A-9E, is coupled to the distal end portion 13 of the housing 12 and encloses the interior space 18 of the housing 12 at the distal end portion of the housing 12. The end cap 50 has a distal end portion 52 and a proximal end portion 53.

The distal end portion 52 has a distal end tip 54, which preferably has a rounded and relatively smooth exterior surface 55 to facilitate insertion and guidance of the primary catheter 10 within a subject. Alternatively, the distal end tip 54 may have a tapered shape for the same purpose. The distal end tip 54 may be formed of or may include a relatively thicker and/or stiffer structure or material compared to the housing 12 to reinforce or provide additional rigidity to the distal end tip 54. The additional rigidity may facilitate inserting and guiding the primary catheter 10 within a subject, and may also reduce or prevent the risk of deformation of the primary catheter 10, for example if an obstruction is encountered. A suitable structure or material may comprise a solid silicon or polyurethane for example. The end cap 50 may be formed as a single integral structure, or may be formed as separate assembled components.

The end cap 50 comprises at least one and preferably a plurality of drain ports 56. Each drain port 56 extends between the interior space 18 and the exterior 15 of the housing 12. The drain ports 56 are adapted for the plurality of drains 36 to pass through the drain ports 56 when the drains 36 are moving and transitioning between the extended position and the retracted position. More specifically, in the example embodiments, each drain port 56 is adapted for one drain 36 to pass through the drain port 56 as the drain 36 is moving and transitioning between the extended position and the retracted position. The plurality of drain ports 56 preferably are spaced apart radially around the periphery of the end cap 50 and are set back slightly (proximally) from the distal end tip 54. The drain ports 56 preferably are sized relatively larger than the diameters of the drains 36 to enable the drains 36 to pass through the drain ports 56 without substantial obstruction or binding.

The end cap 50 also comprises at least one and preferably a plurality of guides 58. The guides 58 are adapted to direct the plurality of drains 36 to pass through the plurality of drain ports 56. Each guide 58 is located in proximity to and just proximal of a corresponding drain port 56. The arrangement of the plurality of drain ports 56 and guides 58 is adapted to cause the plurality of drains 36 to extend radially outwardly at acute angles from the housing 12 to the exterior 15 of the housing 12 through the drain ports 56 when the plurality of drains 36 are in the extended position.

Preferably each guide 58 comprises a surface 59 that extends at an angle and is adapted to engage and guide a drain 36 through the corresponding drain port 56 at approximately the same angle. The guide 58 may comprise an angled ramp for example. In the example embodiment, the surface 59 extends from an outer edge 57 of the corresponding drain port 56 in a proximal and inward direction toward the interior space 18 of the housing 12. In the example embodiment, the surface 59 comprises a conic section of the rounded distal end tip 54 and is therefore somewhat rounded. Alternatively, the surface 59 may be made planar or frusto-conical, or may comprise another type of conic-section.

In operation, as a drain 36 moves within the single lumen 30 in the direction of the distal end portion 13 of the housing 12 in transition to the extended position, the distal end portion 44 of the drain 36 exits the single lumen 30, enters the end cap 50, and contacts the angled surface 59 of the corresponding guide 58. The surface 59 redirects the motion of the drain 36 toward the corresponding drain port 56. Further motion of the drain 36 then results in the distal end portion 42 of the drain 36 passing through the drain port 56 and outwardly to the exterior 15 of the housing 12 at approximately the angle of the surface 59, as shown in FIG. 7B for example.

Because the drains 36 in the extended position extend through the drain ports 56 outwardly at angles that are approximately the same as the angles of the surfaces 59 of the guides 58 relative to the housing 12, the spacing of the drain ports 56 around the end cap 50 and the angles of the surfaces 59 may be selected to determine the directions the drains 36 will extend from the housing, how far apart the distal end portions 42 of the drains 36 will be spaced, and the direction and spacing of the locations that will be irrigated and/or drained, as well as the overall extent of the area to which the drains 36 will provide irrigation and drainage.

The end cap 50 also comprises a guidewire passage 62, an internal guidewire opening 63 in the proximal end portion 53 of the end cap 50, and an external guidewire opening 64 in the distal end tip 54 of the end cap 50. The guidewire passage 62 extends through the end cap 50 from the internal guidewire opening 63 to external guidewire opening 64. The internal guidewire opening 63 is exposed to the interior space 18 of the housing 12 and the exterior guidewire opening 64 is exposed to the exterior 15 of the housing 12. The guidewire passage 62 is adapted to receive and enable a guidewire (not shown) to pass through the end cap 50 between the internal guidewire opening 63 and the external guidewire opening 64.

In use, a guidewire may be inserted through the common drain 32 and advanced through the guidewire passage opening 89 of the internal connector 70 described below, the single lumen 30, and the guidewire passage 62 of the end cap 50 into a desired space or location of a subject in which the primary catheter 10 is to be inserted to provide irrigation and/or drainage. The primary catheter 10 may then be advanced over the guidewire to the desired location, under radiological image guidance for example, or by manipulating a stylet 100 as described below after the guidewire has been removed.

In an embodiment wherein the housing 12 is in the form of an elongated cylinder with a longitudinal axis, the end cap 50 may be substantially aligned with the longitudinal axis of the housing 12 and with the common drain 32 and the space comprising the single lumen 30. The guidewire passage 62 of the end cap 50 may be substantially on the longitudinal axis of the housing 12 and may be substantially aligned along the longitudinal axis of the housing 12 with the stylet passage 86 of the internal connector 70 described below.

The end cap 50 also comprises at least one and preferably a plurality of stop projections 66. The stop projections 66 project from the proximal end portion 53 of the end cap 50 in the direction of the proximal end portion 14 of the housing 12 for a short distance but do not extend into the single unpartitioned lumen 30. In the example embodiment, the plurality of stop projections 66 are radially spaced around the guidewire passage 62 and the internal guidewire opening 63 with each stop projection 66 being located between two adjacent guides 58 and corresponding drain ports 56.

Each of the stop projections 66 includes a stop surface 67. Each stop surface 67 preferably faces at least partially in the direction of the proximal end portion 14 of the housing 12 and is exposed to the space comprising the single lumen 30. The stop surfaces 67 are adapted to engage the distal end surface 75 of the internal connector 70 described below as the internal connector 70 moves toward the distal end portion 13 of the housing 12 and reaches the distal-most extent of its range of travel within the single lumen 30. The locations of the stop surfaces 67 thus define the furthest distal position within the single lumen 30 to which the internal connector 70 may move. Preferably, the stop surfaces 67 are arranged and configured so that when the distal end surface 75 of the internal connector 70 contacts the stop surfaces 67, a small length of the proximal end portions 38 of the drains 36 and the holding bars 77 of the internal connector 70, which are described below, remain within the primary catheter 10 and do not extend to the exterior 15 of the housing 12.

Each of the stop projections 66 also includes a pair of oppositely facing lateral guide surfaces 68. Each of the lateral guide surfaces 68 extends from a location in proximity to a corresponding guide 58 and corresponding drain port 56 in the direction of the proximal end portion 14 of the housing 12 and terminates at a stop surface 67. The lateral guide surfaces 68 are adapted to engage and guide the distal end portions 42 of the drains 36 in the end cap 50 as the distal end portions 42 advance distally in the end cap 50 toward the guides 58 and drain ports 56 as the drains 36 move toward and into the extended position.

G. Internal Connector.

The primary catheter 10 comprises an internal connector 70. The internal connector 70, details of which are illustrated in FIGS. 10A-10E, has a proximal end portion 72, a proximal end surface 73, a distal end portion 74, a distal end surface 75, and an exterior surface 76. In embodiments in which the housing 12 of the primary catheter 10 is in the form of an elongated cylinder with a longitudinal axis and/or the interior space 18 of the housing 12 comprising the single lumen 30 is substantially cylindrical and symmetric with the longitudinal axis of the housing 12, the internal connector 70 also suitably may be formed in the shape of an elongated cylinder. In that case, the internal connector 70 may also have a longitudinal axis that is substantially coaxial with the longitudinal axis of the housing 12 and/or the space comprising the single lumen 30. The internal connector 70 preferably is formed of a solid, relatively rigid material, which may be a suitable plastic for example.

The internal connector 70 is configured, adapted and dimensioned to be enclosed within the housing 12 within the single lumen 30 and to be selectively movable within the single lumen 30 substantially between the proximal end portion 14 of the housing 12 and the distal end portion 13 of the housing 12. As described above, the internal connector 70 is movable within the single lumen 30 toward the distal end portion of the housing 12 until the distal end surface 75 of the internal connector 70 reaches a position in contact with one or more stop surfaces 67 of the end cap 50. The internal connector 70 is movable within the single lumen 30 toward the proximal end portion 14 of the housing 12 at least until the proximal end surface 73 of the internal connector 70 reaches the common drain 32. If desired, the internal connector 70 may be configured and adapted to be entirely removable from the primary catheter 10 by being movable first in the direction of the proximal end portion 14 of the housing 12 within the single lumen 30 and then movable past the proximal end portion 14 of the housing 12 through the common drain 32.

The plurality of drains 36 preferably are coupled to the internal connector 70 with the proximal end portions 38 of the drains 36 removably coupled to the distal end portion 74 of the internal connector 70, the distal end portions 42 of the drains 36 extending into the single lumen 30 in the direction of the distal end portion 13 of the housing 12, and the drains 36 spaced radially around the distal end portion 74 of the internal connector 70 as illustrated in FIGS. 7A, 8A, 12A, and 14A for example.

More specifically, the internal connector 70 has a plurality of holding bars 77 that extend from the distal end portion 74 and more specifically the distal end surface 75 of the internal connector 70 toward the distal end portion 74 of the housing 12 and slightly into the single lumen 30. The holding bars 77 are adapted to engage and to removably couple the plurality of drains 36 to the internal connector 70 in a manner described below.

The holding bars 77 may be formed as a single structure with the internal connector 70 as illustrated in FIGS. 10A-10E, or may be formed separately and connected to the internal connector 70 in a suitable fashion. In the example embodiments, four holding bars 77 are radially and equidistantly spaced around the distal end portion 74 of the internal connector 70 at approximately 90 degree intervals and each holding bar 77 has two adjacent holding bars 77 on either side of it. It will be appreciated however that the foregoing represents but one possible arrangement of the holding bars 77 and that both the number and arrangement of the holding bars 77 may be varied.

Figure 12A:
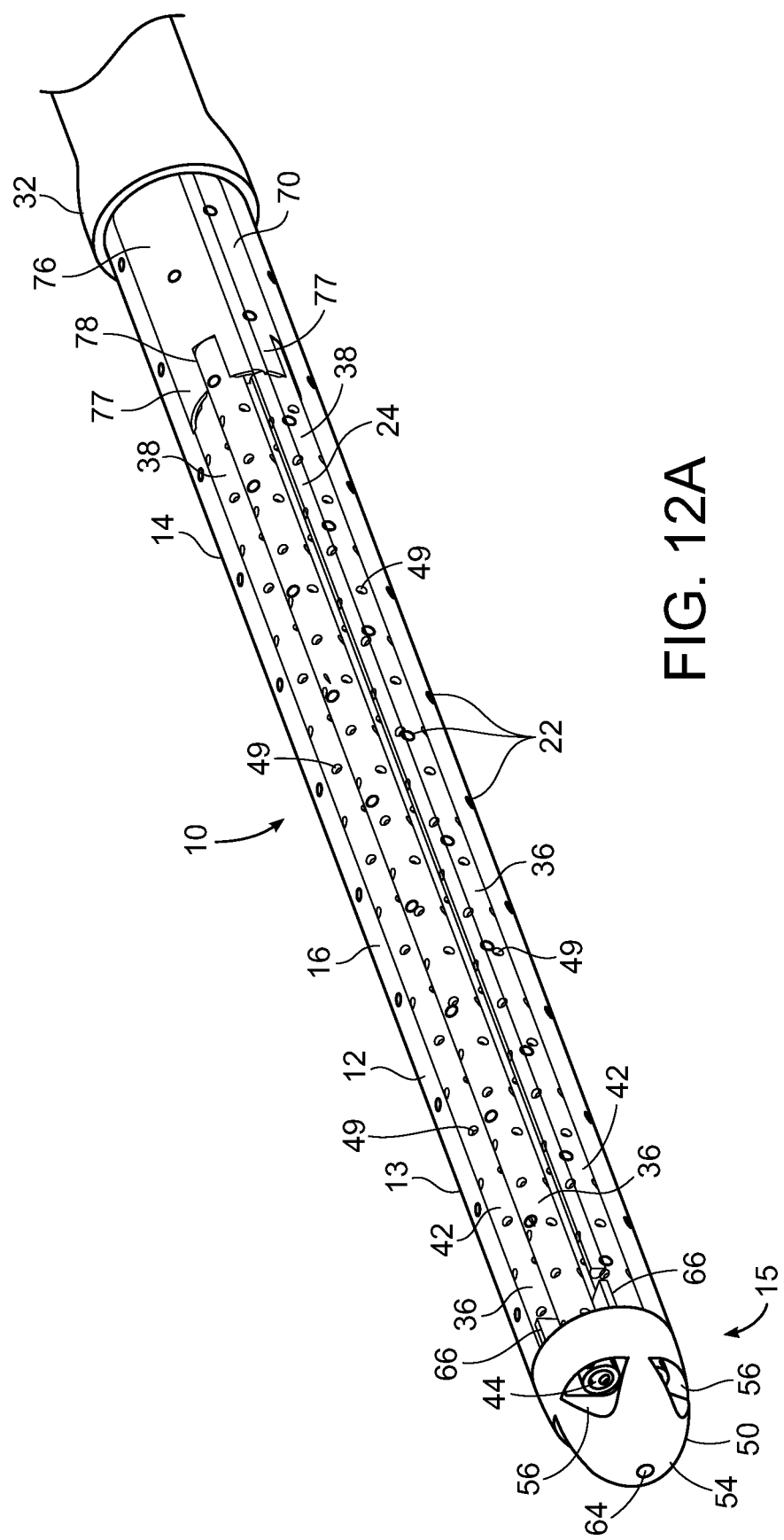
FIG. 12A is a partially transparent perspective view of a single lumen drainage catheter with extendable and retractable drains in accordance with an example embodiment.
Figure 12B:
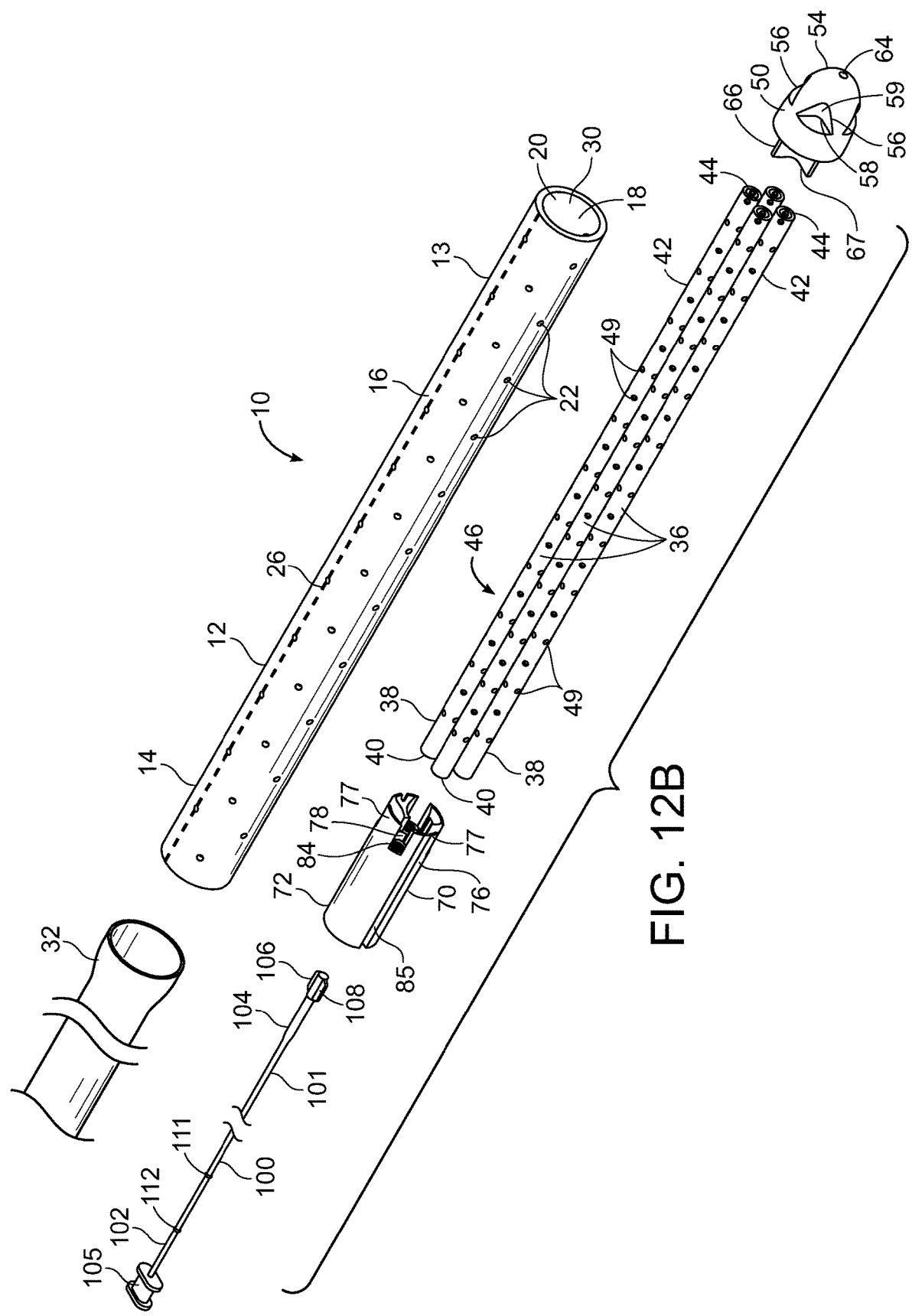
FIG. 12B is an exploded perspective view of a single lumen drainage catheter with extendable and retractable drains and a stylet for use with the catheter in accordance with an example embodiment.

Each pair of adjacent holding bars 77 and the space between them defines a drain bay 78. Each drain bay 78 is configured and adapted to receive, engage and hold a drain 36 between the pair of adjacent holding bars 77. Thus, depending on the number and arrangement of holding bars 77 the internal connector 70 may have one or more drain bays 78. Each holding bar 77 of the pair of adjacent holding bars 77 of a drain bay 78 has at least one drain engagement surface 79. In the example embodiments, each holding bar 77 more preferably has two drain engagement surfaces 79, each substantially facing and in proximity to one of two adjacent holding bars 77. The drain engagement surfaces 79 are configured and adapted to engage the exterior surface of the proximal end portion 38 of a drain 36 received in the drain bay 78 and to removably couple the drain 36 to the internal connector 70. Each drain bay 78 is thus preferably configured and adapted to engage and hold a drain 36 between a pair of adjacent holding bars 77 in at least two spaced apart locations on the exterior surface of the drain 36 for example as seen in FIGS. 8A and 12A.

The geometric shapes of the drain engagement surfaces 79 of the holding bars 77 may vary depending on the shape of the drains 36. In the example embodiments wherein the drains 36 are preferably in the shape of elongated cylindrical tubes, the drain engagement surfaces 79 of the holding bars 77 preferably comprise curvilinear surfaces that are adapted to engage and removably hold a drain 36 in a drain bay 78.

The internal connector 70 also comprises at least one and preferably a plurality of drain passages 82 each of which extends through the internal connector 70 between the proximal end surface 73 and the distal end surface 75 of the internal connector 70. Each drain passage 82 has a proximal drain passage opening 83 in the proximal end surface 73 of the internal connector 70 and a distal drain passage opening 84 in the distal end surface 75 of the internal connector 70. The proximal drain passage openings 83 and the distal drain passage openings 84 may comprise one or a plurality of openings, for example in the form of a grate as seen in FIGS. 10A-10E particularly. The grate configuration is preferred to avoid inadvertently catching the distal end tip 106 of the stylet 100 described below in a proximal or distal drain passage opening 83, 84 when the stylet 100 is being manipulated to engage and move the internal connector 70 within the single lumen 30 of the housing 12 as described below.

In the example embodiments, the drain passages 82 preferably are radially spaced apart in the internal connector 70 with their corresponding proximal drain passage openings 83 being radially spaced apart in the proximal end surface 73 of the internal connector 70 and their corresponding distal drain passage openings 84 being radially spaced apart in the distal end surface 75 of the internal connector 70. Preferably the distal drain passage openings 84 are arranged and spaced so that each distal drain passage opening 84 is positioned in a drain bay 78 between a pair of adjacent holding bars 77. Alternatively stated, the holding bars 77 preferably are arranged so that each drain bay 78 defined by a pair of holding bars 77 is aligned with and adjacent to a distal drain passage opening 84. Accordingly, each drain bay 78 is adapted to engage and hold a drain 36 between a pair of adjacent holding bars 77 with the proximal end portion opening 40 of the drain 36 aligned with and adjacent to a distal drain passage opening 84.

The drain passages 82 are adapted for fluid to flow through them and hence through the internal connector 70 between their corresponding distal drain passage openings 84 and corresponding proximal drain passage openings 83. The drain passages 82 are in fluid communication with the plurality of drains 36 via the distal drain passage openings 84 and more specifically in the example embodiments, each drain passage 82 is in fluid communication with one drain 36. The drain passages 82 also are in fluid communication with the common drain 32 via the proximal drain passage openings 83. Hence, the drain passages 82 are adapted for fluid to flow through them and through the internal connector 70 between the drains 36 and the common drain 32.

With the drains 36 coupled to the internal connector 70 as described above, movement of the internal connector 70 in the single lumen 30 between the proximal end portion 14 of the housing 12 and the distal end portion 13 of the housing 12 causes the plurality of drains 36 to move between the retracted position as illustrated for example in FIGS. 7A, 8A, and 12A and the extended position as illustrated for example in FIG. 7B. The internal connector 70 is caused to move within the single lumen 30 to move the drains 36 between the retracted and extended positions by remote manipulation of the stylet 100 in engagement with the internal connector 70 as described below.

The internal connector 70 has an exterior surface 76 that extends between the proximal end portion 72 and the distal end portion 74 of the internal connector 70 and more specifically the proximal end surface 73 and the distal end surface 75 of the internal connector 70. The exterior surface 76 includes an engagement element 85. The engagement element 85 is configured and adapted to be in moveable engagement with the corresponding engagement element 24 on the interior surface 20 of the housing 12 as the internal connector 70 moves within the single lumen 30 in the interior space 20 of the housing 12 between the proximal end portion 14 and the distal end portion 13 of the housing 12. The engagement element 85 is configured and adapted to mutually engage with the corresponding engagement element 24 so as to maintain a fixed angular alignment between the internal connector 70 and the housing 12 and to prevent the internal connector 70 from rotating as the internal connector 70 moves within the housing 12.

Figure 10B:
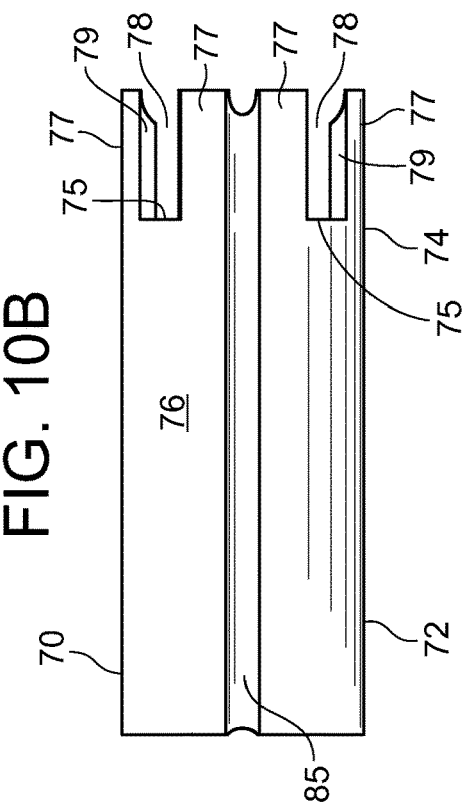
FIG. 10B is a side view of an internal connector of a single lumen drainage catheter with extendable and retractable drains in accordance with an example embodiment.
Figure 10E:
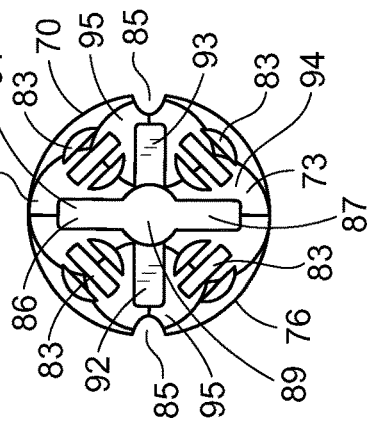
FIG. 10E is a proximal end portion view of an internal connector of a single lumen drainage catheter with extendable and retractable drains in accordance with an example embodiment.
Figure 10D:
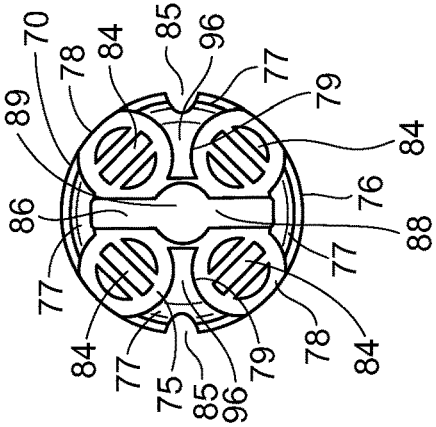
FIG. 10D is a distal end portion view of an internal connector of a single lumen drainage catheter with extendable and retractable drains in accordance with an example embodiment.
Figure 10A:
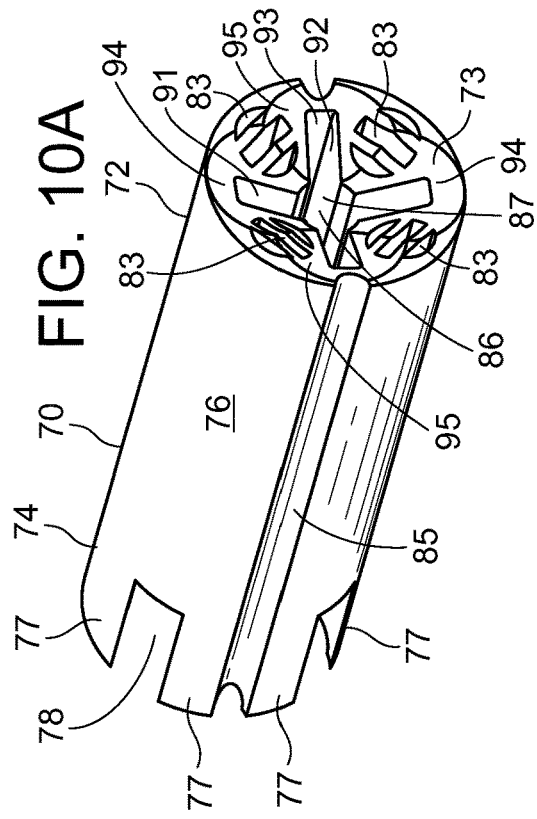
FIG. 10A is a perspective view of an internal connector of a single lumen drainage catheter with extendable and retractable drains in accordance with an example embodiment.
Figure 10C:
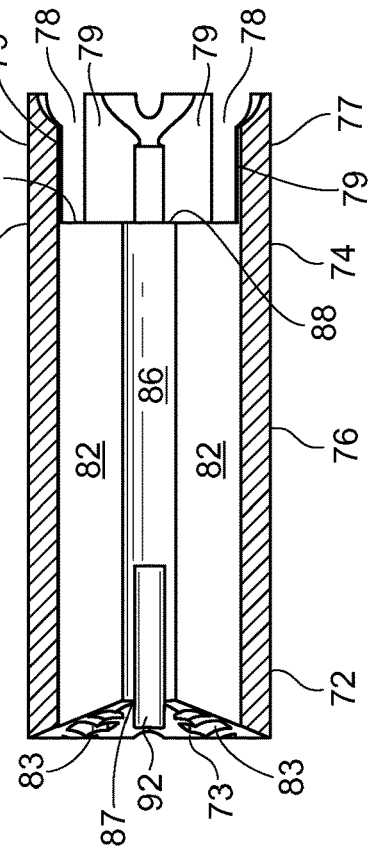
FIG. 10C is a cross-sectional side view of an internal connector of a single lumen drainage catheter with extendable and retractable drains in accordance with an example embodiment.
Figure 11A:
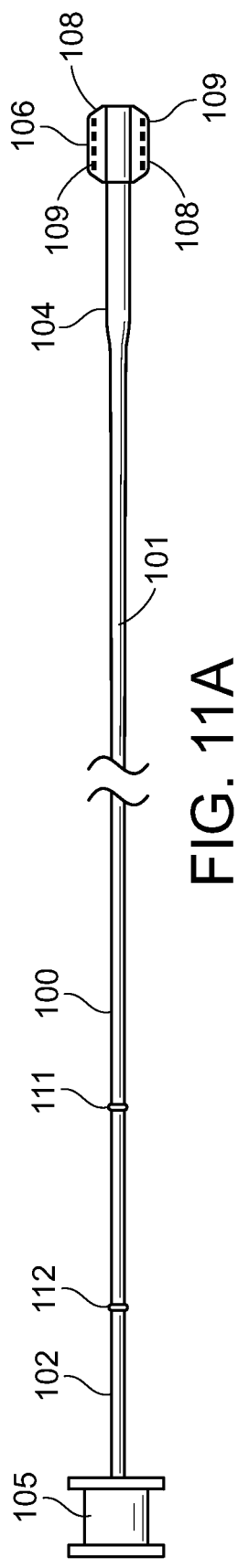
FIG. 11A is a side view of a stylet for use with a single lumen drainage catheter with extendable and retractable drains in accordance with an example embodiment.
Figure 11B:
FIG. 11B is another side view of the stylet illustrated in FIG. 11A rotated by 90 degrees.
Figure 11C:
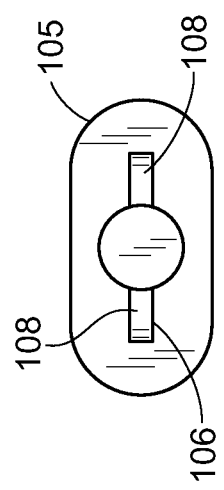
FIG. 11C is a distal end view of a stylet for use with a single lumen drainage catheter with extendable and retractable drains in accordance with an example embodiment.

The engagement element 85 may comprise one element or a plurality of elements spaced about the exterior surface 76 of the internal connector 70. For example two elements could be spaced apart opposite each other on opposite sides of the exterior surface 76 as illustrated in FIGS. 10A and 10E. Preferably, the engagement element 85 will extend longitudinally along the exterior surface 76 of the internal connector 70 substantially the entire distance between the proximal end surface 73 and the distal end surface 75 of the internal connector 70. The engagement element 85 may comprise an indent in the exterior surface such as an elongated groove as seen in FIGS. 10A and 10B for example. Alternatively, the engagement element 85 may comprise a protrusion such as an elongated rib, and may also comprise a protrusion or indent having a variety of shapes suitable for the stated purpose. It will be appreciated that whatever the shape, number, and location(s) of the engagement element 85 on the exterior surface 76 of the internal connector 70, the engagement element 85 should correspond with and be complimentary with the engagement element 24 on the interior surface 20 of the housing 12 so that the engagement elements 24 and 85 are maintained in moveable engagement and prevent rotation of the internal connector 70 as it moves within the housing 12.

The internal connector 70 also comprises a stylet passage 86. The stylet passage 86 extends through the internal connector 70 between the proximal end surface 73 and the distal end surface 75. The stylet passage has a stylet passage proximal opening 87 in the proximal end surface 73 and a stylet passage distal opening in the distal end surface 75. The stylet passage 86, the stylet passage proximal opening 87, and the stylet passage distal opening 88 have a first shape and a first orientation and are configured and adapted to allow the distal end tip 106 of the stylet 100 described below to enter and pass through the stylet passage 86 when the distal end tip 106 is aligned with the stylet passage 86, the stylet passage proximal opening 87, and the stylet passage distal opening 88 in the first orientation and to prevent the distal end tip 106 from passing through the stylet passage 86 when the distal end tip 106 is not aligned with the stylet passage 86, the stylet passage proximal opening 87, and the stylet passage distal opening 88 in the first orientation. The stylet passage 86 and the distal end tip 106 are thus configured and adapted so that the stylet 100 can be remotely manipulated to remotely cause the distal end tip 106 of the stylet 100 to selectively pass through or to selectively engage the internal connector 70.

In the example embodiment, the first shape includes a guidewire passage opening 89. The guidewire passage opening 89 is preferably substantially centered in the proximal end surface 73 and the distal end surface 75 of the internal connector 70 and is preferably positioned substantially coaxial with the longitudinal axis of the internal connector 70 and the housing 12 of the primary catheter 10 when the internal connector 70 is disposed in the single lumen 30 within the housing 12. The guidewire passage opening 89 is preferably, but not necessarily, cylindrical in shape and defines a passage for a guidewire (not shown) to pass through the internal connector 70 and between the proximal and distal end portions 13, 14 of the housing 12 of the primary catheter 10 in either direction. Preferably also, the guidewire passage opening 89 is substantially coaxial with the internal guidewire opening 63, the external guidewire opening 64, and the guidewire passage 62 of the end cap 50 to facilitate the guidewire being passed through the end cap 50 of the primary catheter 10 to a location within a subject where the primary catheter 10 is to be positioned.

The first shape also preferably comprises a first elongated slot 91 and the first orientation comprises an orientation wherein the first slot 91 extends approximately through, perpendicular to, and centered on the longitudinal axis of the internal connector 70 between two pairs of adjacent drain passages 82 and corresponding proximal and distal drain passage openings 83, 84. However, it will be appreciated that the first shape can also take other forms, for example, a star or other geometric shape, or an alphanumeric shape. Similarly, the first orientation can be varied, for example being offset from the longitudinal axis of the internal connector 70, provided the stylet passage 86 does not interfere substantially with the functioning of the drain passages 82.

The internal connector 70 also includes a stylet engagement opening 92. The stylet engagement opening 92 is formed in the proximal end surface 73 of the internal connector 70. The stylet engagement opening 92 extends partially into the internal connector 70 but does not pass completely through the internal connector 70. The stylet engagement opening 92 is configured and adapted to selectively receive, be entered by and be engaged by the distal end tip 106 of the stylet 100. The stylet engagement opening 92 preferably has a second shape and a second orientation for that purpose. The stylet engagement opening 92 is thus configured and adapted to permit the distal end tip 106 to enter the stylet engagement opening 92 when the distal end tip 106 is aligned with the stylet engagement opening 92 in the second orientation, and to prevent the distal end tip 106 from being received by and entering the stylet engagement opening 92 when the distal end tip 106 is not aligned with the stylet engagement opening 92 in the second orientation. The stylet engagement opening 92 preferably has a relatively shallow depth to lock the distal end tip 106 of the stylet 100 in the internal connector 70 in a "push" position.

The stylet engagement opening 92 and the distal end tip 106 are thus configured and adapted so that the stylet 100 can be remotely manipulated to cause the distal end tip 106 of the stylet 100 to selectively engage the proximal end portion 72 of the internal connector 70, to push the internal connector 70, and to cause the internal connector 70 to move within the single lumen 30 of the housing 12 in a direction toward the distal end portion 13 of the housing 12 when the distal end tip 106 is in the stylet engagement opening 92.

In the example embodiment, the second shape comprises a second elongated slot 93 that is substantially the same shape as the first slot 91 and that includes the same guidewire passage 89 as the first slot 91. The second orientation of the second slot 93 is preferably angularly offset from the first orientation of the first slot 91 such that the first slot 91 and the second slot 93 cross or intersect. Preferably, but not necessarily, the first orientation and the second orientation are offset substantially at 90 degree angles or perpendicular. In the second orientation, like the first orientation, the second slot 93 extends approximately through, perpendicular to, and centered on the longitudinal axis of the internal connector 70 between two pairs of adjacent drain passages 82 and corresponding proximal and distal drain passage openings 83, 84. Thus, the first slot 91 and the second slot 93 intersect on the longitudinal axis of and in the center of the proximal end surface 73 of the internal connector 70. However, it will be appreciated that the second shape can also take other forms, for example, a star, or an alphanumeric shape. Similarly, the second orientation can be varied, for example being offset from the longitudinal axis of the internal connector 70, provided the stylet engagement opening 92 does not interfere substantially with the functioning of the drain passages 82. It will also be appreciated that the second shape need not be the same as the first shape. For example, the first shape could comprise a slot and the second shape could comprise a star or other geometric shape.

The proximal end surface 73 of the internal connector 70 is preferably formed as and comprises a frusto-conical shape that slopes inwardly from the proximal edges of the exterior surface 76 toward the center of the proximal end surface 73 of the internal connector 70. The frusto-conical shape facilitates remotely manipulating the stylet 100 to position the distal end tip 106 of the stylet 100 selectively in the stylet passage proximal opening 87 or the stylet engagement opening 92. The frusto-conical shape also helps guide the distal end of a guidewire, if used, into the guidewire passage opening 89.

In addition, the proximal end surface 73 of the internal connector 70 preferably comprises a first directing surface 94 that is adapted to engage the distal end tip 106 of the stylet 100 and direct the distal end tip 106 into the stylet passage proximal opening 87 and a second directing surface 95 that is adapted to engage the distal end tip 106 of the stylet 100 and direct it into the stylet engagement opening 92. Each of the first directing surface 94 and the second directing surface 95 comprises an additional conic section formed within the frusto-conical shape of the proximal end surface 73. In the example embodiment, the first directing surface 94 comprises a pair of oppositely disposed conic section surfaces with half of the slot of the stylet passage proximal opening 87 formed in each conic section surface, and the second directing surface comprises a pair of oppositely disposed conic section surfaces with half of the slot of the stylet engagement opening 92 formed in each conic section surface. Adjacent conic section surfaces intersect and form a raised ridge 96 between them which further facilitates directing the distal end tip 106 of the stylet 100 selectively into the stylet passage proximal opening 87 or the stylet engagement opening 92. The first directing surface 94 and the second directing surface 95 also help guide the distal end of a guidewire, if used, into the guidewire passage opening 89.

The internal connector 70 also includes a stylet engagement surface 96. The stylet engagement surface 96 is formed on the distal end surface 75 of the internal connector 70. In the example embodiments, the stylet engagement surface 96 is formed as an extension of two oppositely disposed holding bars 77 as illustrated in FIG. 13B. However, it will be appreciated that the stylet engagement surface 96 may be formed directly on the distal end surface 75 if desired.

The stylet engagement surface 96 is configured and adapted to selectively be engaged by the distal end tip 106 of the stylet 100. The stylet engagement surface 96 preferably has a third shape and a third orientation for that purpose. The stylet engagement surface 96 is thus configured and adapted to permit the distal end tip 106 to engage the stylet engagement surface 96 when the distal end tip 106 is aligned with the stylet engagement surface 96 in the third orientation, and to prevent the distal end tip 106 from engaging the stylet engagement surface 96 when the distal end tip 106 is not aligned with the stylet engagement surface 96 in the third orientation. The stylet engagement surface 96 and the distal end tip 106 are thus configured and adapted so that the stylet 100 can be remotely manipulated to cause the distal end tip 106 of the stylet 100 to selectively engage the distal end portion 74 of the internal connector 70, to pull the internal connector 70, and to remotely cause the internal connector 70 to move within the single lumen 30 in the housing 12 in a direction toward the proximal end portion 14 of the housing when the distal end tip 106 is engaged with the stylet engagement surface 96.

In the example embodiment, the third shape of the stylet engagement surface 96 comprises an elongated relatively narrow surface. The stylet engagement surface 96 is preferably split or interrupted to accommodate passage of the distal end tip 106 and stylet 100 through the internal connector 70 and the single lumen 30 within the housing 12 of the primary catheter 10. In the example embodiments, the stylet engagement surface 96 as well as the distal end surfaces of the holding bars 77 are sloped inwardly from the distal edges of the exterior surface 76 of the internal connector 70 toward the center of the distal end surface 75 of the internal connector 70 to facilitate manipulation of the stylet 100 to align the distal end tip 106 with the second orientation of the distal drain passage opening 84 of the internal connector 70.

The third orientation of the stylet engagement surface 96 is preferably, but not necessarily, the same as the second orientation of the stylet engagement opening 92 on the proximal and distal end surfaces 73, 75 of the internal connector 70. That is, the third orientation preferably is angularly offset from the first orientation of the first slot 91 of the stylet passage distal opening 88 at a substantially 90 degree angle. But for the stylet engagement surface 96 being interrupted, it would extend approximately through, perpendicular to, and centered on the longitudinal axis of the internal connector 70 between two pairs of adjacent distal drain passage openings 84 of drain passages 82 and corresponding adjacent drain bays 78. However, it will be appreciated that the third shape of the stylet engagement surface 96 can also take other forms that are continuous or interrupted, and similarly that the third orientation can be different from the second and third orientation as described above, provided the stylet engagement surface 96 does not interfere substantially with the movement of the distal end tip 106 and the stylet 100 through the internal connector 70 or with the functioning of the drain passages 82.

Although the internal connector 70 has been described above in the context of having a plurality of drains 36 coupled thereto, it will be appreciated that the internal connector 70 can have coupled thereto other elongated tools or elements in addition to, in combination with, or in place of drains 36. Such other elongated tools or elements can include, for example, one or more tubes, mechanical and/or electrical probes, electrodes, remote cameras, illumination elements, and/or other tools or elements to be contained within the single lumen 30 of the primary catheter 10 when in a retracted position for insertion and positioning within a subject and to extend outwardly to the exterior 15 of the primary catheter 10 when in an extended position for use within the subject. Such other tools or elements can be adapted, for example, to deliver medicaments, to deliver electrical energy, to sense electrical signals, to engage and interact with tissue of the subject, to provide visual and/or mechanical feedback, etc. Further, the other tools or elements can be selectively coupled to the internal connector 70 in various combinations depending on the needs of a particular procedure. For one example, one or more electrodes and electrical probes can be coupled to the internal connector 70 at spaced locations. For another example, one or more tubes, one or more drains 36, and one or more cameras and/or illumination elements can be coupled to the internal connector 70.

The other tools or elements are preferably removably coupled to the internal connector 70 in the same manner as described above with respect to the drains 36. That is, the other tools or elements have proximal end portions that are adapted to be removably engaged and held by the holding bars 77 in the same manner as described with respect to the drains 36 such that the other tools or elements are spaced around the distal end portion 74 of the internal connector 70 with the distal end portions of the other tools or elements extending into the single lumen 30 in the direction of the distal end portion 13 of the housing 12.

In the case of other tools or elements that are not drains and/or that do not involve a flow of fluid, the plurality of drain passages 82 through the internal connector 70 between the proximal end surface 73 and the distal end surface 75 can be configured to carry wires, etc. Thus, for example, electrical wires for remote cameras, illumination elements, electrodes, and probes can be fed through the drain passages 82 of the internal connector 70. Alternatively, the drain passages 82 can be replaced with dedicated conduits for wires or the like. Further, in the case of other tools or elements that are not drains and/or that do not involve flow of fluid, the drain bays 78 of the internal connector 70 can be thought of as tool bays in which the other tools or elements are seated in engagement with the internal connector 70 since no fluids are intended to flow through these other tools or elements and the drain passages 82 corresponding to those tool bays.

With the other tools or elements coupled to the internal connector 70 as described above, movement of the internal connector 70 in the single lumen 30 between the proximal end portion 14 of the housing 12 and the distal end portion 13 of the housing 12 causes the other tools or elements to move between the retracted position in which they are contained within the single lumen 30 and the extended position in which at least their distal ends extend outwardly from the housing 12 to the exterior 15 of the primary catheter 10 through the drain ports 56 in the same manner as described herein with respect to the drains 36. The internal connector 70 is caused to move within the single lumen 30 to move the drains 36 between the retracted and extended positions by remote manipulation of the stylet 100 in engagement with the internal connector 70 in the same manner as described herein with respect to the drains 36.

H. Stylet.

An elongated stylet 100 is designed to be used with the primary catheter 10. The stylet 100 can be remotely manipulated as described further below to facilitate the insertion and location of the primary catheter 10 in a subject and to move the drains 36 between the retracted position and the extended position.

With reference to the drawings, and more particularly FIGS. 12B-15B, the stylet 100 has an elongated shaft 101 with a proximal end portion 102 and a distal end portion 104. A handle 105 is connected to or formed as part of the proximal end portion 102 and a distal end tip 106 is connected to or formed as part of the distal end portion 104. The shaft 101 is suitably made of a relatively rigid material such as steel, or a somewhat more flexible material such as braided steel fibers. The shaft 101 may have various lengths depending on the dimensions of the primary catheter 10 with which the stylet 100 is to be used and the distance to the location within a subject the primary catheter 10 is to be positioned.

The distal end tip 106 has a fourth shape that is configured and adapted to correspond and cooperate with the first, second and third shapes of the stylet passage proximal and distal openings 87, 88 of the stylet passage 86, the stylet engagement opening 92, and the stylet engagement surface 96 of the internal connector 70 as described above. The distal end tip 106 thus effectively constitutes a key and the first, second, and third shapes constitute corresponding key openings or key acceptance mechanisms.

More specifically, in the example embodiments, the distal end tip 106 comprises one or more protrusions 108. The protrusions 108 preferably extend radially outward from the distal end tip 106 and are arranged on the distal end tip 106 so that the stylet 100 can be manipulated to selectively place the distal end tip 106 and more specifically the protrusions 108 in a first orientation aligned with the stylet passage proximal and distal openings 87, 88 of the stylet passage 86, in a second orientation aligned with the stylet engagement opening 92, and in a third orientation aligned with the stylet engagement surface 96 of the internal connector 70.

The protrusions 108 preferably are shaped so that when selectively oriented in the first orientation aligned with the shape of the stylet passage proximal and distal openings 87, 88 of the stylet passage 86, the distal end tip 106 and stylet 100 are able to enter and pass through the internal connector 70 through the stylet passage 86. Conversely, when not oriented in the first orientation, the shape of the protrusions 108 and the shape of the stylet passage proximal and distal openings 87, 88 of the stylet passage 86 prevent the distal end tip 106 from entering the stylet passage proximal and distal openings 87, 88 and passing through the stylet passage 86.

Similarly, when the protrusions 108 are selectively oriented in the second orientation aligned with the shape of the stylet engagement opening 92, the distal end tip 106 is able to enter into and engage the stylet engagement opening 92 in the proximal end surface 73 of the proximal end portion 72 of the internal connector 70. Conversely, when not oriented in the second orientation, the shape of the protrusions 108 and the shape of the stylet engagement opening 92 prevent the distal end tip 106 from entering and engaging the stylet engagement opening 92.

Also similarly, when the protrusions 108 are selectively oriented in the third orientation aligned with the shape of the stylet engagement surface 96, the distal end tip 106 is able to engage the stylet engagement surface 96. Conversely, when not oriented in the third orientation, the shape of the protrusions 108 and the shape of the stylet engagement surface 96 prevent the distal end tip 106 from engaging the stylet engagement surface 96.

Still more specifically, in the example embodiments, wherein the first and second shapes of the stylet passage proximal and distal openings 87, 88 and the stylet engagement opening 92 are elongated slots, and the third shape of the stylet engagement surface 96 is an elongated and relatively narrow surface, the protrusions 108 preferably comprise relatively thin, substantially planar protrusions or bits that extend radially outward in substantially opposite directions, i.e., radially spaced by approximately 180 degrees. It will be appreciated that in other embodiments where the first, second, and third shapes are different than described herein, the shape of the distal end tip 106 will be modified accordingly. It will also be appreciated that the first, second and third shapes, and the corresponding fourth shape of the distal end tip 106 can be almost any corresponding shapes consistent with achieving the purposes and objectives described herein.

As will be appreciated from the foregoing and the additional description below, the stylet 100 is adapted to be remotely manipulated to move the distal end tip 106 within the single lumen 30 in the housing 12 and to selectively cause the distal end tip 106 to pass through the internal connector 70 to engage and move the primary catheter 10. The stylet 100 also is adapted to be remotely manipulated to move the distal end tip 106 within the single lumen 30 in the housing 12 to selectively cause the distal end tip 106 to engage the internal connector 70 and selectively move the internal connector 70 within the single lumen 30 between a first position at which the plurality of drains 36 are in the retracted position and a second position at which the plurality of drains 36 are in the extended position. More specifically, the stylet 100 is adapted to be remotely manipulated to move the internal connector 70 in a direction toward the distal end portion 13 of the housing 12 when the distal end tip 106 is in the stylet engagement opening 92 to cause the drains 36 to move from the retracted position toward and into the extended position. The stylet 100 is adapted to be remotely manipulated to move the internal connector 70 in a direction toward the proximal end portion 14 of the housing 12 when the distal end tip 106 is engaged with the stylet engagement surface 96 to cause the drains 36 to move from the extended position toward and into the retracted position.

The stylet 100 and the distal end tip 106 can be remotely manipulated by a user or operator using the handle 105 at the proximal end portion 102 of the shaft 101. The user may use the handle 105 remote from and externally to the primary catheter 10 to insert the distal end tip 106 of the stylet 100 through the common drain 32 into the primary catheter 10 and to retract the distal end tip 106 from the primary catheter 10 through the common drain 32. The user may also use the handle 105 to remotely advance and retract the distal end tip 106 through the internal connector 70 and within the housing 12, and more specifically the single lumen 30, of the primary catheter 10 between the proximal and distal end portions 13, 14 of the housing 12. The user also may rotate the handle 105 to remotely rotate the distal end tip 106 within the primary catheter 10, and more particularly within the single lumen 30 in the housing 12 of the primary catheter 10. The handle 105 preferably has a diameter or width dimension greater than the diameter or width dimension of the opening in the common drain 32 leading into the housing 12 of the primary catheter 10 to prevent the handle 105 from entering the primary catheter 10.

In order to insert and position the primary catheter 10 through body tissue or a tract of a subject to a desired space or location for irrigation and/or drainage, a guidewire may first be inserted into the subject and an end of the guidewire positioned at or near the desired location within the subject. The primary catheter 10 may then be inserted on the guidewire with the guidewire extending through the guidewire passage 62 of the end cap 50, the single lumen 30 in the housing 12, the stylet passage 86 of the internal connector 70 and the common drain 32. The primary catheter 10 may be manually guided on the guidewire to the desired location. Once the primary catheter 10 is at or near the desired location, the guidewire may be removed. Alternatively, it may not be necessary to use a guidewire, and the primary catheter 10 may be inserted into and positioned within the subject remotely under control of the stylet 100.

The stylet 100 can be remotely manipulated using the handle 105 to insert and position the primary catheter 10 within a subject in the following manner. The stylet 100 is remotely manipulated to insert the distal end tip 106 into the primary catheter 10 through the common drain 32 (see FIG. 14A). The stylet 100 is then remotely manipulated to rotate the distal end tip 106 into an orientation in alignment with stylet passage proximal opening 87 (FIG. 13A) and is further remotely manipulated to advance the distal end tip 106 through the stylet passage 86 of the internal connector 70 (FIG. 13B), though the single lumen 30 and into engagement with the proximal end portion 53 of the end cap 50 (FIG. 14A) at the distal end portion 13 of the housing 12. The stylet 100 can be further remotely manipulated to advance the distal end tip 100 and hence to move the primary catheter 10 in the direction shown by the arrow in FIG. 14A to move the primary catheter 10 into and/or within the subject to the desired space or location to be irrigated and/or drained.

Once the primary catheter 10 is in the desired position, the stylet 100 is remotely manipulated to retract the distal end tip 106 back through the lumen 30 and the internal connector 70. If necessary, the handle 105 of the stylet 100 can be rotated to rotate the distal end tip 106 into an orientation in alignment with the stylet passage distal opening 88 of the internal connector 70 in order to retract the distal end tip 106 through the internal connector 70.

It will be appreciated that while the primary catheter 10 is being inserted and positioned within a subject, the drains 36 will be in a first retracted position enclosed within the single lumen 30 in the housing 12 of the primary catheter 10. Once the primary catheter 10 in position, the stylet 100 can be remotely manipulated to cause the drains 36 to move from the retracted position to a second extended position wherein they extend to the exterior 15 of the housing 12. The stylet 100 can be remotely manipulated to cause the drains 36 to move into the extended position in the following manner.

With the distal end tip 106 inserted through the common drain 32, the stylet 100 is remotely manipulated using the handle 105 to advance the distal end tip 106 into proximity with the proximal end surface 73 of the internal connector 70 and to rotate the distal end tip 106 into an orientation in alignment with the stylet engagement opening 92 (FIG. 13C). The stylet 100 is then remotely manipulated to advance the distal end tip 106 into the stylet engagement opening 92 where it is in engagement with the internal connector 70. In this first position of the internal connector 70, the drains 36 are in the fully retracted position completely enclosed within the housing 12.

With the distal end tip 106 in the stylet engagement opening 92, the stylet 100 is remotely manipulated to push or advance the distal end tip 106 toward the distal end portion 13 of the housing 12. This causes the internal connector 70 and the drains 36 to advance in the lumen 30 of the housing 12 toward the distal end portion 13 of the housing 12 (FIGS. 13D, 14B). As the stylet 100 is remotely manipulated to continue to advance the distal end tip 106, the internal connector 70, and the drains 36 toward the distal end portion 13 of the housing 12, the distal end portions 42 of the drains 36 advance through the end cap 50, engage the guide surfaces 59 of the guides 58, and are directed distally and radially outwardly from the housing 12 through the drain ports 56 at acute angles (FIGS. 2, 4, 7B, 14B). The stylet 100 is remotely manipulated to continue to push the distal end tip 106, the internal connector 70, and the drains 36 to advance toward the distal end portion 13 of the housing 12 until the distal end surface 75 of the internal connector 70 contacts the stop surfaces 67 of the stop projections 66 on the proximal end portion 52 of the end cap 50 (FIG. 7B). This defines the furthest extent to which the internal connector 70 can travel within the single lumen 30 in the direction of the distal end portion 13 of the housing 12. In this second position of the internal connector 70, the drains 36 are in the fully extended position.

With the drains 36 in the extended position and the common drain 32 connected to a drainage reservoir or irrigation source, fluid can flow between the exterior 15 of the housing 12 by a plurality of paths as described above. When it is desired to discontinue the irrigation and/or draining, and/or to remove the primary catheter 10 from the subject, the stylet 100 can be remotely manipulated using the handle 105 to cause the drains 36 to move into the retracted position in the following manner.

The stylet 100 is remotely manipulated to cause the distal end tip 106 to align with the stylet passage proximal opening 87 of the internal connector 70 and is further manipulated to advance the distal end tip 106 through the stylet passage 86 of the internal connector 70 in the manner described above (FIGS. 13A, 13B). The handle 105 of the stylet 100 is then rotated to bring the distal end portion 106 into an orientation in alignment with the stylet engagement surface 96 on the distal end portion 74 of the internal connector 70. The stylet 100 is then remotely manipulated to pull or retract the distal end tip 106 into engagement with the stylet engagement surface 96 (FIG. 13E). With the distal end tip 106 in engagement with the stylet engagement surface 96, the stylet 100 is remotely manipulated to pull or retract the distal end tip 106 in the direction of the proximal end portion 14 of the housing 12 (FIG. 13E). This causes the internal connector 70 and the drains 36 to retract in the lumen 30 of the housing 12 toward the proximal end portion 14 of the housing 12 (FIG. 14C). As the stylet 100 is remotely manipulated to continue to retract the distal end tip 106, the internal connector 70, and the drains 36 toward the proximal end portion 13 of the housing 12, the drains 36 retract through the drain ports 56 of the end cap 50 into the single lumen 30 in the housing 12 (FIG. 14C). The stylet 100 is remotely manipulated to continue to pull and retract the distal end tip 106, the internal connector 70, and the drains 36 toward the proximal end portion 14 of the housing 12 until the proximal end surface 73 of the internal connector 70 contacts the common drain 32 (FIG. 7A). This defines the furthest extent to which the internal connector 70 can travel within the single lumen 30 in the direction of the proximal end portion 13 of the housing 12. In this first position of the internal connector 70, the drains 36 are in the fully retracted position enclosed within the single lumen 30 in the housing 12 (FIGS. 7A, 8A, 12A).

Once the drains 36 are in the fully retracted position, the stylet 100 can continue to be remotely manipulated to further pull the distal end tip 106 in the direction of the proximal end portion 14 of the housing 12. Since the internal connector 70 cannot move further proximally relative to the housing 12, this causes the primary catheter 10 to be pulled proximally from its location in the subject and thus can be used to reposition the primary catheter 10 or to remove the primary catheter 10 from the subject. In order to remove the stylet 100 entirely, the handle 105 can be rotated to bring the distal end tip 106 into alignment with the stylet passage distal opening 88 in the distal end surface 75 of the internal connector 70 and then manipulated to retract the distal end tip 106 through the stylet passage 86 of the internal connector 70 and out of the primary catheter 10 through the common drain 32.

To facilitate remotely orienting and aligning the distal end tip 106 of the stylet 100 with the stylet passage proximal and distal openings 87, 88, the stylet engagement opening 92, and the stylet engagement surface 96 of the internal connector 70, the distal end tip 106 preferably includes alignment markers 109. The alignment markers 109 are configured and adapted to be employed together with the alignment marker 26 on the exterior surface 16 of the housing 12 to provide a remote visual indication of the orientation and alignment of the distal end tip 106 relative to the stylet passage proximal and distal openings 87, 88, the stylet engagement opening 92, and the stylet engagement surface 96. Preferably the alignment markers 109 comprise a material or substance that is substantially radio-opaque. This enables the alignment markers 109 to provide a remote visual indication of orientation and alignment when the primary catheter 10 is within a subject and being positioned remotely under the visual guidance provided by radio-imaging equipment.

In the example embodiments, the alignment markers 109 are provided on or near the outer lateral extents or peripheries of each of the outwardly extending protrusions 108 of the distal end tip 106 for example as shown in FIGS. 11A, 13A-13C, 13E, and 15A-15B. The alignment markers 109 extend in the longitudinal direction of and preferably substantially parallel with the elongated shaft 101 of the stylet 100.

More specifically, the alignment markers 109 are configured and adapted to be aligned with the corresponding alignment marker 26 on the housing 12 in a first alignment in which the distal end tip 106 is in a first orientation aligned with the stylet passage proximal and distal openings 87, 88 of the internal connector 70 and able to pass through the internal connector 70, and in a second alignment in which the distal end tip 106 is in a second orientation aligned with the stylet engagement opening 92 and/or the stylet engagement surface 96 of the internal connector 70 and able to engage the internal connector 70 and move it within the lumen 30 of the housing 12 between the distal end portion 13 and the proximal end portion 14 of the housing 12. In the example embodiments, in the first alignment the alignment markers 109 are in line with alignment marker 26 on the housing 12 and together form a single line (FIG. 15A). In the second alignment, the alignment markers 109 are on either side of the alignment marker 26 on the housing 12 and form three substantially parallel lines (FIG. 15B). Thus, the markers 109 and marker 26 are adapted and configured to provide a clear remote visual indication of the alignment and orientation of the distal end tip 106 relative to the internal connector 107 within the housing 12. It will be appreciated that while the markers 109 and 26 are linear, other non-linear marker types could be used to visually indicate the first and second alignment such as a reticle, a gradation scale, etc.

To facilitate remote manipulation of the stylet 100 to move the internal connector 70 between the first and second positions and the drains 36 between the corresponding retracted and extended positions, the stylet 100 has a first level marker 111 and a second level marker 112. The first and second level markers 111, 112 are formed as part of or are connected to the shaft 101 of the stylet 100. The first and second level markers 111, 112 are adapted and configured to provide a remote visual indication to a user or operator manipulating the stylet 100 of the distance or level to which the distal end tip 106 of the stylet 100 has been inserted within the primary catheter 10 and specifically the distance or level the distal end tip 106 has been inserted with respect to the internal connector 70.

More specifically, the first level marker 111 is adapted and configured to provide a remote visual indication when the distal end tip 106 has been inserted to a first distance or level at which the distal end tip 106 is in engagement with the internal connector 70 and the internal connector 70 is in its first position with the drains 36 in the retracted position. The second level marker 112 is adapted and configured to provide a remote visual indication when the distal end tip 106 has been inserted to a second distance or level at which the distal end tip 106 has pushed or moved the internal connector 70 to its second position with the drains 36 in the extended position. The first and second level markers 111, 112 thus facilitate manipulation of the stylet 100 to selectively engage and move the internal connector 70 and the drains 36 within the lumen 30 of the housing 12 between the retracted and extended positions as described above.

It is preferred that the first level marker 111 and the second level marker 112 each extend substantially around the periphery of the shaft 101 of the stylet 100. This enables the markers to continue to provide a remote visual indication even when the stylet 100 is rotated. Accordingly, the first level marker 111 and the second level marker 112 each may be cylindrical in shape or some other shape depending on the cross-sectional shape of the shaft 101 of the stylet 100. Alternatively, the first and second level markers 111, 112 can take the form of painted points or bars, and/or can comprise grooves, indentations, or any other form that can provide a remote visual indication of the distance or level of insertion of the distal end tip 106 of the stylet 100 in the primary catheter 10, specifically with respect to the internal connector 106.

In order to provide a remote visual indication when the distal end tip 106 has been inserted to a first distance or level where the internal connector 70 is in the first position and to a second distance or level where the internal connector 70 is in the second position, both as described above, the first level marker 111 and the second level marker 112 are spaced apart longitudinally on the shaft 101 at selected locations. The locations are selected to correspond to the distances the distal end tip 106 must be inserted in and retracted from the primary catheter 10 in engagement with the internal connector 70 for the internal connector to be in the first position with the drains 36 fully retracted (first level marker 111) and in the second position with the drains fully extended (second level marker 112). The proximal end of the common drain 32 may be used as a reference with the first and second level markers 111, 112 to visually gauge the distance or level to which the distal end tip 106 has been inserted, for example as illustrated in FIGS. 15A-15B. It will be apparent to persons skilled in the art that the selection of the relative locations on the shaft 101 of the stylet 100 for the first and second level markers 111, 112 will depend on a number of variables, including the relative length dimensions of the primary catheter 10, the internal connector 70, and the drains 36, the desired degree of extension of the drains 36, and others.

I. Operation of Preferred Embodiment.

An example use of the example embodiments is described below with reference to FIGS. 16 and 17.

FIG. 16 illustrates an example embodiment integrated within a ventriculoperitoneal shunt system. The ventricle 115 is a cavity within the brain 116 that is naturally filled with cerebrospinal fluid 117. However, an excess accumulation of cerebrospinal fluid 117 can lead to a condition known as hydrocephalus. To drain excess cerebrospinal fluid 117 from an affected ventricle 115, the stylet 100 is used in the manner described herein to insert the primary catheter 10 into the ventricle 115. The primary catheter 10 may be inserted through a burr hole drilled in the skull of the subject and advanced through the subject's brain tissue until the all or a portion of the distal end portion 13 of the primary catheter 10 resides within the ventricle 115.

Once the distal end portion 13 is located within the ventricle 115, the stylet 100 is used in the manner described previously to extend the drains 36 outwardly from the housing 12 of the primary catheter 10 to a plurality of spaced apart locations within the ventricle 115 cavity. The proximal end portion 14 of the primary catheter 10 traverses the brain 116 and is connected to a valve 118 that functions to regulate fluid drainage pressure. The valve 118 is in turn connected to a shunt catheter 119 that typically is routed to the subject's peritoneal cavity.

Upon opening the valve 118, the excess cerebrospinal fluid 117 is simultaneously drained from a number of spaced apart locations in the affected ventricle 115 through a plurality of fluid flow paths in the primary catheter 10. The excess cerebrospinal fluid 117 flows into the distal end portion openings 44 of the drains 36, through the plurality of openings 49 from the exterior 46 to the interior space 48 of the drains 36, through the plurality of openings 22 in the housing 12 of the primary catheter 10, through the lumen 30, through the drain passage openings 83, 84 and drain passages 82 in the internal connector 70 and into the common drain 32. From the common drain 32 the fluid flows through the valve 118 and shunt catheter 119 to the subject's peritoneal cavity, from where it can be drained or absorbed in the subject's blood stream.

FIG. 17 illustrates an example embodiment integrated within a peritoneal dialysis system. In peritoneal dialysis, the dialysis fluid is introduced from outside a subject's body into the subject's peritoneal cavity 120 via a catheter. During a prescribed dwell time, fluids and waste products pass from the subject's bloodstream into the dialysis fluid. At the end of the dwell time, the dialysis fluid containing the waste products is allowed to drain from the peritoneal cavity through the catheter.

The stylet 100 is used in the manner described herein to insert the primary catheter 10 into the subject's peritoneal cavity 120. The primary catheter 10 may be inserted into the subject through an incision near the subject's umbilicus and advanced through the subject's abdominal wall 121 until all or a portion of the distal end portion 13 of the primary catheter 10 resides within the peritoneal cavity 120. Once the distal end portion 13 is located within the peritoneal cavity 120, the stylet 100 is used in the manner described previously to extend the drains 36 outwardly from the housing 12 into a plurality of spaced apart locations within the peritoneal cavity 120. The proximal end portion 14 of the housing 12 of the primary catheter 10 passes through the incision and the subject's abdominal wall 121. A cuff 122 can be positioned around the distal end portion 13 of the housing 12, preferably within the abdominal wall 121. The cuff 122 is made of non-absorbable fibers that promote tissue fibrosis and adhesion formation in order to help hold the primary catheter 10 in place for a potentially lengthy period of time. Outside the subject's body the proximal end portion 14 of the housing 12 is connected to peritoneal dialysis tubing 123 via an adapter 124.

Once the peritoneal dialysis system is in place, dialysis fluid is introduced into and drained from the plurality of spaced apart locations in the subject's peritoneal cavity 120 simultaneously through a plurality of fluid flow paths in the primary catheter 10. The dialysis fluid flows between the proximal end portion 14 of the housing 12 of the primary catheter 10 and the subject's peritoneal cavity 120 through the common drain 32, which in this case also is a common irrigation inlet, proximal and distal drain passage openings 83, 84 and drain passages 82 of the internal connector 70, the proximal and distal end portion openings 40, 44 of the plurality of drains 36, the plurality of openings 49 between the exterior 46 and the interior space 48 of the plurality of drains 36, the lumen 30, and the plurality of openings 22 in the housing 12. During introduction of dialysis fluid into the peritoneal cavity 120, the fluid is introduced into and flows through the peritoneal dialysis tubing 123, the common drain 132 (common irrigation inlet) and the proximal end portion 14 of the housing 12 of the primary catheter 10, into the distal end portion 13 of the housing 12 of the primary catheter 10, and through the aforementioned plurality of paths into the subject's peritoneal cavity 120.

After the prescribed dwell period, the dialysis fluid is drained from the peritoneal cavity 120 through the same plurality of openings and flow paths in the distal end portion 13 of the housing 12 to the proximal end portion 14 of the housing 12, through the common drain 32, and then through the dialysis tubing 123 into a drainage container or reservoir for disposal.

Unless otherwise defined, all technical and scientific terms used herein have the same meaning as commonly understood by one of ordinary skill in the art to which this invention belongs. Although specific terms are employed herein, they are used in a generic and descriptive sense only and not for purposes of limitation. Any headings utilized within the description are for convenience only and have no legal or limiting effect. All publications, patent applications, patents, and other references mentioned herein are incorporated by reference in their entirety to the extent allowed by applicable law and regulations.

Although methods and materials similar to or equivalent to those described herein can be used in the practice or testing of the drainage catheter with retractable internal drains, suitable methods and materials are described above. The drainage catheter with retractable internal drains may be embodied in other specific forms without departing from the spirit or essential attributes thereof, and it is therefore desired that the present embodiments be considered in all respects as illustrative and not restrictive. Therefore, it is to be understood that the invention is not to be limited to the specific embodiments disclosed but is to be accorded the scope defined by the language of the appended claims consistent with the concepts, principles, and features disclosed herein.

What is claimed is:

1. A catheter, comprising:
    a primary drainage catheter comprising a housing with a common drain, the primary drainage catheter providing continuous fluid drainage from a patient;
    wherein the housing has a distal end portion, a proximal end portion, an exterior, and an interior space comprising a single unpartitioned lumen;
    wherein the common drain is coupled to the proximal end portion of the housing and is adapted for a fluid to flow through the common drain, wherein the common drain is attached the exterior portion of the housing; and
    a plurality of drains arranged within the single unpartitioned lumen with each drain of the plurality of drains having a proximal end, a distal end, and an interior space between the proximal end and the distal end, wherein each drain of the plurality of drains is adapted for the fluid to flow through the interior space between the proximal end and the distal end;
    wherein the common drain is in fluid communication with the single unpartitioned lumen of the interior space of the housing and with the plurality of drains;
    wherein the plurality of drains are adapted to be movable within the single unpartitioned lumen between an extended position with at least the distal end portions of the plurality of drains extending to the exterior of the housing and a retracted position with the plurality of drains being enclosed within the single unpartitioned lumen of the housing; and
    wherein with the plurality of drains in the extended position the plurality of drains provide a first plurality of paths for the fluid to flow between the common drain and the exterior of the housing;
    an internal connector having a proximal end portion, a proximal end surface, a distal end portion, and a distal end surface, wherein:
    the internal connector is enclosed within the single unpartitioned lumen and is selectively movable within the single unpartitioned lumen substantially between the proximal end portion of the housing and the distal end portion of the housing;
    the plurality of drains are coupled to the internal connector with the proximal ends of the plurality of drains coupled to the distal end portion of the internal connector and the distal end of the drains extending into the single unpartitioned lumen; and
    movement of the internal connector between the proximal end portion of the housing and the distal end portion of the housing causes the plurality of drains to move between the retracted position and the extended position; and,
    an elongated stylet having a proximal end portion, a distal end portion, and a distal end tip.

2. The catheter of claim 1, wherein the housing comprises a first plurality of openings, wherein the first plurality of openings are adapted for the fluid to flow through the first plurality of openings between the exterior of the housing and the single unpartitioned lumen, and wherein the first plurality of openings provide a second plurality of paths for the fluid to flow between the common drain and the exterior of the housing.

3. The catheter of claim 2, wherein the first plurality of openings are spaced apart along the housing substantially the entire distance between the proximal end portion of the housing and the distal end portion of the housing.

4. The catheter of claim 1, wherein the single unpartitioned lumen extends substantially the entire distance between the proximal end portion of the housing and the distal end portion of the housing.

5. The catheter of claim 1, wherein at least one drain of the plurality of drains has a second plurality of openings, and wherein when the plurality of drains are in the extended position the second plurality of openings are adapted for the fluid to flow between the interior space of the drain and the exterior of the housing to provide a third plurality of paths for the fluid to flow between the common drain and the exterior of the housing.

6. The catheter of claim 1, wherein at least one drain of the plurality of drains comprises a tube with the distal end of the drain and the proximal end of the drain being open to the interior space of the drain.

7. The catheter of claim 1, comprising an end cap coupled to the distal end portion of the housing, wherein the end cap comprises a plurality of drain ports that extend between the interior space and the exterior of the housing and that are adapted for the plurality of drains to pass through when moving between the extended position and the retracted position.

8. The catheter of claim 7, wherein the end cap comprises a plurality of guides that are adapted to direct the plurality of drains to pass through the plurality of drain ports.

9. The catheter of claim 8, wherein the plurality of guides comprise a plurality of angled ramps.

10. The catheter of claim 8, wherein the plurality of drain ports and the plurality of guides are arranged to cause the plurality of drains to extend outwardly from the housing at acute angles when the plurality of drains are in the extended position.

11. The catheter of claim 1, wherein the plurality of drains are spaced around the distal end portion of the internal connector.

12. The catheter of claim 11, wherein the plurality of drains are radially spaced around the distal end portion of the internal connector.

13. The catheter of claim 1, wherein:
the internal connector comprises a plurality of drain passages that extend through the internal connector between the proximal end surface and the distal end surface;
the plurality of drain passages are in fluid communication with the plurality of drains and with the common drain and are adapted for the fluid to flow through them between the plurality of drains and the common drain.

14. The catheter of claim 13, wherein each drain passage of the plurality of drain passages is in fluid communication with one drain of the plurality of drains.

15. The catheter of claim 13, wherein the internal connector comprises a plurality of holding bars that extend from the distal end portion of the internal connector into the single unpartitioned lumen and are adapted to engage and hold the plurality of drains.

16. The catheter of claim 15, wherein each drain passage has a drain passage opening, wherein the plurality of holding bars are arranged with a pair of holding bars defining a drain bay adjacent to each drain passage opening, and wherein each drain bay is adapted to engage and hold a drain of the plurality of drains between the pair of holding bars comprising the drain bay with the proximal end of the drain aligned with the drain passage opening.

17. The catheter of claim 16, wherein at least one drain bay is adapted to engage and hold a drain of the plurality of drains between the pair of holding bars comprising the drain bay in at least two spaced apart locations on the drain.

18. The catheter of claim 16, wherein at least one drain of the plurality of drains is substantially cylindrical in shape and wherein at least one pair of holding bars comprising a drain bay each comprises a curvilinear surface adapted to engage and hold the at least one drain.

19. The catheter of claim 1, wherein:
the internal connector has an exterior surface that extends between the proximal end portion of the internal connector and the distal end portion of the internal connector;
the housing has an interior surface that extends between the proximal end portion of the housing and the distal end portion of the housing;
the exterior surface of the internal connector comprises a first engagement element;
the interior surface of the housing comprises a second engagement element; and
wherein the first engagement element and the second engagement element are adapted to be in movable engagement as the internal connector is moved within the single unpartitioned lumen between the proximal end portion and the distal end portion of the housing.

20. The catheter of claim 19, wherein the first engagement element comprises an elongated groove and the second engagement element comprises an elongated rib.

21. The catheter of claim 19; wherein:
the internal connector comprises:
a stylet passage that extends through the internal connector between the proximal end surface of the internal connector and the distal end surface of the internal connector, wherein the stylet passage has a first shape and a first orientation;
a stylet engagement opening in the proximal end surface of the internal connector, wherein the stylet engagement opening has a second shape and a second orientation; and
a stylet engagement surface on the distal end surface of the internal connector, wherein the stylet engagement surface has a third shape and a third orientation;
wherein the distal end tip has a fourth shape and the stylet is adapted to be manipulated to selectively place the distal end tip in the first orientation, the second orientation and the third orientation;
wherein the first shape and the fourth shape are configured so that the distal end tip is able to pass through the stylet passage when the distal end tip is in the first orientation and the distal end tip is not able to pass through the stylet passage when the distal end tip is not in the first orientation;
wherein the second shape and the fourth shape are configured so that the distal end tip is able to enter the stylet engagement opening when the distal end tip is in the second orientation, and the distal end tip is not able to enter the stylet engagement opening when the distal end tip is not in the second orientation;
wherein the third shape and the fourth shape are configured so that the distal end tip is able to engage the stylet engagement surface when the distal end tip is in the third orientation, and the distal end tip is not able to engage the stylet engagement surface when the distal end tip is not in the third orientation; and wherein
the stylet is adapted to be manipulated:
to move the internal connector in a direction toward the distal end portion of the housing when the distal end tip is in the stylet engagement opening;
to move the internal connector in a direction toward the proximal end portion of the housing when the distal end tip is engaged with the stylet engagement surface.

22. The catheter of claim 21, wherein the first shape comprises a first slot, the second shape comprises a second slot, and the first slot and the second slot cross with the first orientation and the second orientation being angularly offset.

23. The catheter of claim 21, wherein the proximal end surface of the internal connector comprises a frusta-conical shape.

24. The catheter of claim 23, wherein the proximal end surface of the internal connector comprises a first directing surface that is adapted to engage the distal end tip of the stylet and direct it into the stylet passage and a second directing surface that is adapted to engage the distal end tip of the stylet and direct it into the stylet engagement slot.

25. The catheter of claim 24, wherein the first directing surface and the second directing surface each comprise a conic section.

\* \* \* \* \*